(12) United States Patent
Samulski et al.

(10) Patent No.: US 7,790,154 B2
(45) Date of Patent: Sep. 7, 2010

(54) DUPLEXED PARVOVIRUS VECTORS

(75) Inventors: Richard Jude Samulski, Chapel Hill, NC (US); Douglas M. McCarty, Chapel Hill, NC (US)

(73) Assignee: The University of North Carolina at Chapel Hill, Chapell Hill, NC (US)

( * ) Notice: Subject to any disclaimer, the term of this patent is extended or adjusted under 35 U.S.C. 154(b) by 797 days.

(21) Appl. No.: 11/655,520

(22) Filed: Jan. 19, 2007

(65) Prior Publication Data

US 2007/0110724 A1 May 17, 2007

Related U.S. Application Data

(62) Division of application No. 10/276,356, filed as application No. PCT/US01/17587 on May 31, 2001, now Pat. No. 7,465,583.

(60) Provisional application No. 60/208,604, filed on Jun. 1, 2000.

(51) Int. Cl.
*C12N 15/86* (2006.01)
*C12N 15/00* (2006.01)
*C12N 15/64* (2006.01)
*A61K 48/00* (2006.01)

(52) U.S. Cl. .................. 424/93.1; 424/93.2; 424/93.21; 424/93.6; 435/456; 435/455; 435/91.4; 435/91.41; 435/91.42

(58) Field of Classification Search ....................... None
See application file for complete search history.

(56) References Cited

U.S. PATENT DOCUMENTS

| 6,057,152 | A | 5/2000 | Samulski et al. | |
|---|---|---|---|---|
| 6,156,303 | A | 12/2000 | Russell et al. | 424/93.2 |
| 6,596,535 | B1 | 7/2003 | Carter | |

FOREIGN PATENT DOCUMENTS

| WO | WO 96/39530 | 12/1996 |
|---|---|---|
| WO | WO 98/48005 | 10/1998 |
| WO | WO 99/11802 A | 3/1999 |
| WO | WO 00/24917 | 5/2000 |
| WO | WO 01/11034 | 2/2001 |
| WO | WO 01/11067 | 2/2001 |

OTHER PUBLICATIONS

Hauswirth et al.; "Adeno-Associated Virus DNA Replication: Nonunit-Length Molecules" *Virology* 93, 57-68 (1979).
Kmiec, E.B. Gene Therapy. May-Jun. 1999. American Scientist, vol. 87, pp. 240-247.
Anderson, W.F., Human Gene Therapy. Apr. 1998. Nature, vol. 392, pp. 25-30.
Verma, I.M. and Somia, N. Gene Therapy- promises, problems and prospect. Sep. 1997. Nature, vol. 389, pp. 239-242.
Meng R.D. and El-Deiry, W.S. Tumor Suppressor Genes as Targets for Cancer Gene Therapy. 1999. Gene Therapy of Cancer, Chapter 1. pp. 3-18.
Wang et al. Adeno-Associated Virus Type 2 DNA Replication in Vivo: Mutation Analyses of the D sequence in Viral Inverted Terminla Repeats, JVI, 1997, vol. 71(4), pp. 3077-3082.
Ryan et al.; "Sequence Requirements for Binding of Rep68 to the Adeno-Associated Virus Terminal Repeats", *Journal of Virology*, 1996, 1542-1553.
Snyder et al.; "Features of the Adeno-Associated Virus Origin Involved in Substrate Recognition by the Viral Rep Protein", *Journal of Virology*, 1993, 6096-6104.
Wang et al.; "A Novel Terminal Resolution-Like Site in the Adeno-Associated Virus Type 2 Genome", *Journal of Virology*, 1997, 1140-1146.
Wang et al.; "Rescue and Replication of Adeno-Associated Virus Type 2 as well as Vector DNA Sequences from Recombinant Plasmids Containing Deletions in the Viral Inverted Terminal Repeats: Selective Encapsidation of Viral Genomes in Progeny Virions", *Journal of Virology*, 1996, 1668-1677.
Wang et al.; "Rescue and Replication Signals of the Adeno-associated Virus 2 Genome", *J. Mol. Biol.*, 1995: 250, 573-580.
Ward et al.; "In Vitro Rescue of an Integrated Hybrid Adeno-associated Virus/Simian Virus 40 Genome", *J. Mol. Biol.*, 1991: 218, 791-804.
Ward et al.; "Short Communication", *Virology*, 1995: 209, 692-695.
Bishop et al., "Role of the Terminal Repeat GAGC Trimer, the Major Rep78 Binding Site, in Adeno-Associated Virus DNA Replication", *Febs Letters*, 397, 1996, p. 97-100.
McCarty et al.; "Adeno-associated virus terminal repeat (TR) mutant generates self-complementary vectors to overcome the rate-limiting step to transduction in vivo", *Gene Therapy*, 2003: 10(26), p. 2112-2118.
Wang et al.; "Adeno-associated virus type 2 DNA replication in vivo: mutational analyses of the D sequence in viral inverted repeats", *Journal of Virology*, 1997: 71(4), p. 3077-3082.
Toulson et al., 42$^{nd}$ Annual Meeting of the American Society of Hematology, San Francisco, CA (Dec. 1-5, 2000). Published in *Blood* 96(11): Part I, p. 432a (Nov. 16, 2000).
McCarty et al., "Self-complementary recombinant adeno-associated virus (scAAV) vectors promote efficient transduction independently of DNA synthesis," *Gene Therapy* 8: 1248-1254 (2001).
Brister et al., "Mechanism of Rep-Mediated Adeno-Associated Virus Origin Nicking," *Journal of Virology* 74(17): 7762-7771 (2000).
Brister et al., "Rep-Mediated Nicking of the Adeno-Associated Virus Origin Requires Two Biochemical Activities, DNA Helicase Activity and Transesterification," *Journal of Virology* 73(11): 9325-9336 (1999).

(Continued)

*Primary Examiner*—Maria Marvich
(74) *Attorney, Agent, or Firm*—Myers Bigel Sibley & Sajovec, PA

(57) ABSTRACT

The present invention provides duplexed parvovirus vector genomes that are capable under appropriate conditions of forming a double-stranded molecule by intrastrand base-pairing. Also provided are duplexed parvovirus particles comprising the vector genome. Further disclosed are templates and methods for producing the duplexed vector genomes and duplexed parvovirus particles of the invention. Methods of administering these reagents to a cell or subject are also described. Preferably, the parvovirus capsid is an AAV capsid. It is further preferred that the vector genome comprises AAV terminal repeat sequences.

46 Claims, 7 Drawing Sheets

OTHER PUBLICATIONS

Chiorini et al., "Cloning and Characterization of Adeno-Associated Virus Type 5," *Journal of Virology* 73(2): 1309-1319 (1999).

de la Maza et al., "Heavy and Light Particles of Adeno-Associated Virus," *Journal of Virology* 33(3): 1129-1137 (1980).

de la Maza et al., "Molecular Structure of Adeno-associated Virus Variant DNA," *The Journal of Biological Chemistry* 3194-3203 (Apr. 10, 1980).

Ferrari et al., "Second-Strand Synthesis is a Rate-Limiting Step for Efficient Transduction by Recombinant Adeno-Associated Virus Vectors," *Journal of Virology* 70(5): 3227-3234 (1996).

Fisher et al., "Transduction with Recombinant Aden-Associated Virus for Gene Therapy is Limited by Leading-Strand Synthesis," *Journal of Virology* 70(1): 520-532 (1996).

Hirata et al., "Design and Packaging of Adeno-Associated Virus Gene Targeting Vectors," *Journal of Virology* 74 (10): 4612-4620 (2000).

Muzyczka, "Use of AAV as a General Transduction Vector for Mammalian Cells," *Current Topics in Microbiology and Immunology* 158: 97-129 (1992).

Snyder et al., "Features of the Adeno-Associated Virus Origin Involved in Substrate Recognition by the Viral Rep Protein," *Journal of Virology* 67(10): 6096-6104 (1993).

Snyder et al., "In vitro Resolution of Covalently Joined AAV Chromosome Ends," *Cell* 60: 105-113 (1990).

Toulson et al., "Production and Improved Transduction Kinetics of Self-Complementary Adeno-Associated Viral Vectors," *Abstract* #1858.

Toulson et al., "Production and Improved Transduction Kinetics of Self-Complementary Adeno-Associated Viral Vectors," *Abstract* #1858, Jan. 2000.

AAV TERMINAL REPEAT AND MUTATIONS TO GENERATE DIMER GENOMES

DUPLEXED PARVOVIRUS VECTORS

RELATED APPLICATION INFORMATION

The present invention is a divisional of U.S. application Ser. No. 10/276,356 (now U.S. Pat. No. 7,465,583 B2, having a filing date of Jan. 21, 2003, which is a 35 U.S.C. §371 national phase application of PCT Application No. PCT/US01/17587, having an international filing date of May 31, 2001, and which claims priority to U.S. Provisional Patent Application No. 60/208,604, filed Jun. 1, 2000, the entire contents of each of which are incorporated by reference herein.

STATEMENT OF FEDERAL SUPPORT

The present invention was made, in part, with the support of grant numbers HL51818, HL 48347, and DK 54419 from the National Institutes of Health. The United States government has certain rights to this invention.

FIELD OF THE INVENTION

The present invention relates to reagents for gene delivery. More particularly, the present invention relates to improved parvovirus-based gene delivery vectors.

BACKGROUND OF THE INVENTION

Adeno-associated virus (AAV) is a nonpathogenic, helper dependent member of the parvovirus family. One of the identifying characteristics of this group is the encapsidation of a single-stranded DNA (ssDNA) genome. In the case of AAV, the separate plus or minus polarity strands are packaged with equal frequency, and either is infectious. At each end of the ssDNA genome, a palindromic terminal repeat (TR) structure base-pairs upon itself into a hairpin configuration. This serves as a primer for cellular DNA polymerase to synthesize the complementary strand after uncoating in the host cell. Adeno-associated virus generally requires a helper virus for a productive infection. Although adenovirus (Ad) usually serves this purpose, treatment of AAV infected cells with UV irradiation or hydroxyurea (HU) will also allow limited replication.

Recombinant AAV (rAAV) gene delivery vectors also package ssDNA of plus or minus polarity, and must rely on cellular replication factors for synthesis of the complementary strand. While it was initially expected that this step would be carried out spontaneously, by cellular DNA replication or repair pathways, this does not appear to be the case. Early work with rAAV vectors revealed that the ability to score marker gene expression was dramatically enhanced when cells were co-infected with adenovirus, or transiently pre-treated with genotoxic agents. This enhancement correlated with the formation of duplex DNA from the single-stranded virion DNA (vDNA). Similar induction of rAAV vectors has been observed in vivo following treatment with Ad, ionizing radiation, or topoisomerase inhibitors. However, the effect was highly variable between different tissues and cell types. It has more recently been suggested that reannealing of complementary vDNA from separate infecting rAAV particles may be an important pathway for rAAV transduction.

The requirement for complementary-strand synthesis, or recruitment, is now considered to be a limiting factor in the efficiency of rAAV vectors. The transduction rate for rAAV in mouse liver has been estimated at approximately 5% of hepatocytes after portal vein infusion of $4.2 \times 10^{10}$ particles. Subsequent experiments revealed that the rAAV vDNA had been taken up into the nuclei of virtually all of the liver hepatocytes, and that the transduction potential of these genomes could be rescued by co-infection with adenovirus. This is consistent with an earlier report of up to 25% of mouse hepatocytes transduced by $10^{10}$ particles of rAAV in the presence of co-infecting adenovirus. Expression from rAAV in liver tissue coincides with the formation of duplex DNA and the vDNA appears to be lost if not converted to duplex within 5-13 weeks. Further experiments suggest that a subpopulation of mouse hepatocytes is transiently permissive for rAAV transduction in vivo.

Accordingly, the present invention addresses a need in the art for improved parvovirus gene delivery vectors. In particular the present invention addresses the requirement for complementary strand synthesis by conventional AAV gene delivery vectors.

SUMMARY OF THE INVENTION

The single-stranded nature of the AAV genome may impact the expression of rAAV vectors more than any other biological feature. Rather than rely on potentially variable cellular mechanisms to provide a complementary-strand for rAAV vectors, it has now been found that this problem may be circumvented by packaging both strands as a single DNA molecule. In the studies described herein, an increased efficiency of transduction from duplexed vectors over conventional rAAV was observed in HeLa cells (5-140 fold). More importantly, unlike conventional single-stranded AAV vectors, inhibitors of DNA replication did not affect transduction from the duplexed vectors of the invention. In addition, the inventive duplexed parvovirus vectors displayed a more rapid onset and a higher level of transgene expression than did rAAV vectors in mouse hepatocytes in vivo. All of these biological attributes support the generation and characterization of a new class of parvovirus vectors (delivering duplex DNA) that significantly contribute to the ongoing development of parvovirus-based gene delivery systems.

Overall, a novel type of parvovirus vector that carries a duplexed genome, which results in co-packaging strands of plus and minus polarity tethered together in a single molecule, has been constructed and characterized by the investigations described herein. Accordingly, the present invention provides a parvovirus particle comprising a parvovirus capsid (e.g., an AAV capsid) and a vector genome encoding a heterologous nucleotide sequence, where the vector genome is self-complementary, i.e., the vector genome is a dimeric inverted repeat. The vector genome is preferably approximately the size of the wild-type parvovirus genome (e.g., the AAV genome) corresponding to the parvovirus capsid into which it will be packaged and comprises an appropriate packaging signal. The present invention further provides the vector genome described above and templates that encode the same.

As a further aspect, the present invention provides a duplexed parvovirus particle comprising: a parvovirus capsid and a vector genome comprising in the 5' to 3' direction: (i) a 5' parvovirus terminal repeat sequence; (ii) a first heterologous nucleotide sequence; (iii) a non-resolvable parvovirus terminal repeat sequence; (iv) a separate heterologous nucleotide sequence that is essentially completely complementary to the first heterologous nucleotide sequence; and (v) a 3' parvovirus terminal repeat sequence; wherein the vector genome is capable under appropriate conditions of intrastrand base-pairing between the heterologous nucleotide sequences upon release from the parvovirus capsid. A double-stranded sequence is formed by the base-pairing between the complementary heterologous nucleotide sequences, which is a suitable substrate for gene expression (i.e., transcription and, optionally, translation) or a substrate for host recombination (i.e., a dsDNA template) in a host cell without the need for host cell machinery to convert the vector genome into a double-stranded form.

The designations of 5' and 3' with respect to the vector genome (or templates for producing the same, see below) does not indicate any particular direction of transcription from the double-stranded sequence formed between the two complementary heterologous sequences. The "coding strand" may be on either the 5' or 3' half of the virion DNA. Those skilled in the art will appreciate that the term "coding strand" is being used in its broadest sense to indicate the strand encoding the desired transcript, and encompasses non-translated sequences as well, including antisense sequences. Thus, transcription may be initiated from the 5' end of the first heterologous nucleotide sequence in the 5' half of the vector genome, or from the 5' end of the complementary heterologous nucleotide sequence on the 3' half of the vector genome.

Alternatively stated, in the double-stranded vDNA formed by intrastrand base-pairing, transcription may be initiated from the open end or from the closed end (i.e., from the end closest to the non-resolvable TR) of the hairpin structure.

According to this embodiment, the parvovirus capsid is preferably an AAV capsid. It is further preferred that the parvovirus terminal repeat sequences and/or the non-resolvable terminal repeat sequences are AAV sequences.

In particular embodiments, the duplexed parvovirus particle comprises sufficient expression control sequences (e.g., a promoter) for expression of the double-stranded sequence formed by intrastrand base-pairing in the self-complementary vDNA.

The vector genome may further express two or more transcripts from the double-stranded sequence formed by intrastrand base-pairing.

As a further aspect, the present invention provides a nucleotide sequence comprising a template for producing a virion DNA, the template comprising a heterologous nucleotide sequence flanked by a parvovirus terminal repeat sequence and a non-resolvable parvovirus terminal repeat sequence.

As a still further aspect, the present invention provides a nucleotide sequence comprising a dimeric template for producing a virion DNA, the template comprising in the 5' to 3' direction: a 5' parvovirus terminal repeat sequence; a first heterologous nucleotide sequence; a non-resolvable parvovirus terminal repeat sequence; a separate heterologous nucleotide sequence that is essentially completely complementary to the first heterologous nucleotide sequence; and a 3' parvovirus terminal repeat sequence; wherein the virion DNA is capable under appropriate conditions of intrastrand base-pairing to form a dsDNA between the heterologous nucleotide sequences upon release from the parvovirus capsid.

Preferably, the parvovirus terminal repeat sequences and/or parvovirus non-resolvable terminal repeat sequences are AAV sequences.

The present invention further provides methods of producing and administering the inventive duplexed parvovirus vectors of the invention. In one particular embodiment, the present invention provides a method of administering a nucleotide sequence to a subject, comprising administering to a subject a duplexed parvovirus particle according to the invention in a pharmaceutically acceptable carrier. Preferably, the duplexed parvovirus particle is administered in a therapeutically-effective amount to a subject in need thereof.

As a further aspect, the present invention provides a method of delivering a nucleotide sequence to a cell, comprising: contacting a cell with a duplexed parvovirus particle comprising: a parvovirus capsid and a vector genome comprising: (i) a 5' parvovirus terminal repeat sequence; (ii) a first heterologous nucleotide sequence; (iii) a centrally-located parvovirus terminal repeat sequence; (iv) a separate heterologous nucleotide sequence that is essentially completely complementary to the first heterologous nucleotide sequence (v) a 3' parvovirus terminal repeat sequence; wherein the duplexed vector genome is capable under appropriate conditions of intrastrand base-pairing between the heterologous nucleotide sequences upon release from the parvovirus capsid.

According to this embodiment, preferably the parvovirus capsid is an AAV capsid, and the vector genome is approximately the size of the wild-type AAV genome. It is further preferred that the parvovirus terminal repeat sequences are AAV sequences. The cell may be contacted with the duplexed parvovirus particle in vitro or in vivo.

These and other aspects of the present invention are described in more detail in the description of the invention set forth below.

DETAILED DESCRIPTION OF THE INVENTION

Figure 1:
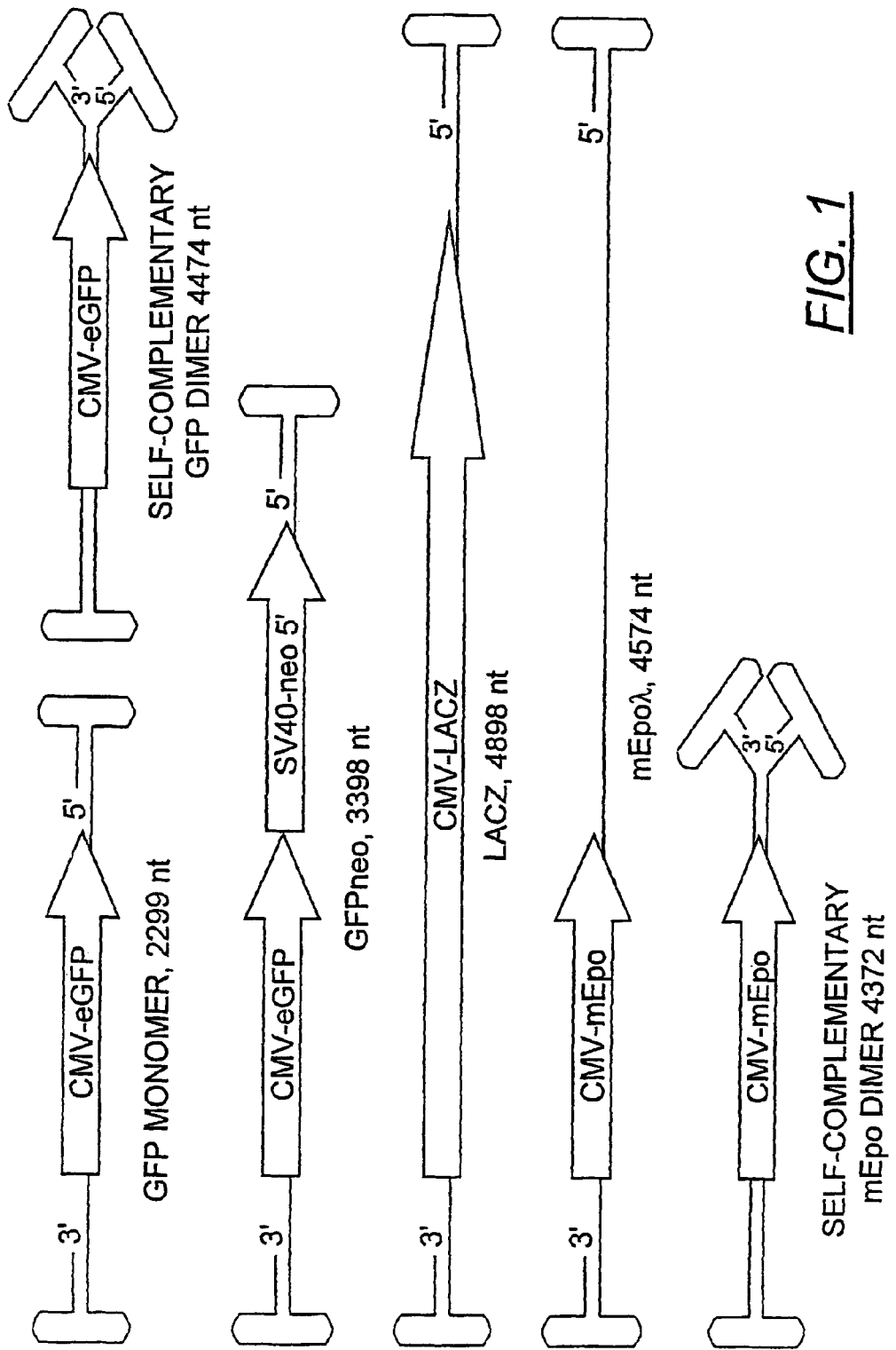
FIG. 1. Virion DNA content of rAAV and duplexed vectors. The drawing illustrates the DNA content of the vectors used in this study and the predicted conformation that they adopt upon release from the virions. The transgenes expressed from the cytomegalovirus immediate early promoter (CMV) are: green fluorescent protein (GFP), β galactosidase (LacZ), mouse erythropoietin (mEpo). Neomycin phosphotransferase (neo) is expressed from the SV40 early promoter (SV40). The size, in nucleotides (nt) of each packaged DNA molecule is indicated. The self-complementary or duplexed (scAAV) GFP dimer and mEpo vectors fold into a complete duplex DNA with one extra copy of the terminal repeat while the GFPneo, LacZ, and mEpoλ vectors require cell-mediated DNA synthesis of the complementary strand.

The present invention will now be described with reference to the accompanying drawings, in which preferred embodiments of the invention are shown. This invention may, however, be embodied in different forms and should not be construed as limited to the embodiments set forth herein. Rather, these embodiments are provided so that this disclosure will be thorough and complete, and will fully convey the scope of the invention to those skilled in the art.

Unless otherwise defined, all technical and scientific terms used herein have the same meaning as commonly understood by one of ordinary skill in the art to which this invention belongs. The terminology used in the description of the invention herein is for the purpose of describing particular embodiments only and is not intended to be limiting of the invention. As used in the description of the invention and the appended claims, the singular forms "a", "an" and "the" are intended to include the plural forms as well, unless the context clearly indicates otherwise. All publications, patent applications, patents, and other references mentioned herein are incorporated by reference in their entirety.

Nucleotide sequences are presented herein by single strand only, in the 5' to 3' direction, from left to right, unless specifically indicated otherwise. Nucleotides and amino acids are represented herein in the manner recommended by the IUPAC-IUB Biochemical Nomenclature Commission, or (for amino acids) by either the one-letter code, or the three letter code, both in accordance with 37 CFR §1.822 and established usage. See, e.g., *PatentIn User Manual*, 99-102 (November 1990) (U.S. Patent and Trademark Office).

Except as otherwise indicated, standard methods known to those skilled in the art may be used for the construction of recombinant parvovirus and rAAV constructs, packaging vectors expressing the parvovirus rep and/or cap sequences, as well as transiently and stably transfected packaging cells. Such techniques are known to those skilled in the art. See, e.g., SAMBROOK et al., MOLECULAR CLONING: A LABORATORY MANUAL 2nd Ed. (Cold Spring Harbor, N.Y., 1989); F. M. AUSUBEL et al. CURRENT PROTOCOLS IN MOLECULAR BIOLOGY (Green Publishing Associates, Inc. and John Wiley & Sons, Inc., New York).

Parvoviruses are relatively small DNA animal viruses and contain a linear, single-stranded DNA genome. The term "parvovirus" as used herein encompasses the family Parvoviridae, including autonomously-replicating parvoviruses and dependoviruses. The autonomous parvoviruses include members of the genera *Parvovirus, Erythrovirus, Densovirus, Iteravirus,* and *Contravirus*. Exemplary autonomous parvoviruses include, but are not limited to, mouse minute virus, bovine parvovirus, canine parvovirus, chicken parvovirus, feline panleukopenia virus, feline parvovirus, goose parvovirus, and B19 virus. Other autonomous parvoviruses are known to those skilled in the art. See, e.g., BERNARD N. FIELDS et al., VIROLOGY, volume 2, chapter 69 (3d ed., Lippincott-Raven Publishers).

The genus *Dependovirus* contains the adeno-associated viruses (AAV), including but not limited to, AAV type 1, AAV type 2, AAV type 3, AAV type 4, AAV type 5, AAV type 6, avian AAV, bovine AAV, canine AAV, equine AAV, and ovine AAV. See, e.g., BERNARD N. FIELDS et al., VIROLOGY, volume 2, chapter 69 (3d ed., Lippincott-Raven Publishers).

As used herein, the term "vector" or "gene delivery vector" may refer to a parvovirus (e.g., AAV) particle that functions as a gene delivery vehicle, and which comprises vDNA (i.e., the vector genome) packaged within a parvovirus (e.g., AAV) capsid. Alternatively, in some contexts, the term "vector" may be used to refer to the vector genome/vDNA.

A "heterologous nucleotide sequence" will typically be a sequence that is not naturally-occurring in the virus. Alternatively, a heterologous nucleotide sequence may refer to a viral sequence that is placed into a non-naturally occurring environment (e.g., by association with a promoter with which it is not naturally associated in the virus).

As used herein, a "recombinant parvovirus vector genome" is a parvovirus genome (i.e., vDNA) into which a heterologous (e.g., foreign) nucleotide sequence (e.g., transgene) has been inserted. A "recombinant parvovirus particle" comprises a recombinant parvovirus vector genome packaged within a parvovirus capsid.

Likewise, a "rAAV vector genome" is an AAV genome (i.e., vDNA) that comprises a heterologous nucleotide sequence. rAAV vectors require only the 145 base terminal repeats in cis to generate virus. All other viral sequences are dispensable and may be supplied in trans (Muzyczka, (1992) *Curr. Topics Microbiol. Immunol.* 158:97). Typically, the rAAV vector genome will only retain the minimal terminal repeat (TR) sequences so as to maximize the size of the transgene that can be efficiently packaged by the vector. A "rAAV particle" comprises a rAAV vector genome packaged within an AAV capsid.

The inventive parvovirus particles may be a "hybrid" particle in which the viral TRs and viral capsid are from different parvoviruses. Preferably, the viral TRs and capsid are from different serotypes of AAV (e.g., as described in international patent publication WO 00/28004, U.S. Provisional Application No. 60/248,920; and Chao et al., (2000) *Molecular Therapy* 2:619; the disclosures of which are incorporated herein in their entireties). Likewise, the parvovirus may have a "chimeric" capsid (e.g., containing sequences from different parvoviruses, preferably different AAV serotypes) or a "targeted" capsid (e.g., a directed tropism) as described in international patent publication WO 00/28004.

Preferably, the inventive duplexed parvovirus particle has an AAV capsid, which may further by a chimeric or targeted capsid, as described above.

The inventive "duplexed" parvovirus particles and vector genomes may interchangeably be referred to herein as "dimeric" or "self-complementary" vectors. The duplexed parvovirus particles of the invention comprise a parvovirus capsid containing a virion DNA (vDNA). The vDNA is self-complementary so that it may form a hairpin structure upon release from the viral capsid. The duplexed vDNA appears to provide to the host cell a double-stranded DNA that may be expressed (i.e., transcribed and, optionally, translated) by the host cell without the need for second-strand synthesis, as required with conventional parvovirus vectors.

The duplexed parvovirus vector genome preferably contains sufficient packaging sequences for encapsidation within the selected parvovirus capsid (e.g, AAV capsid).

Those skilled in the art will appreciate that the duplexed vDNA may not exist in a double-stranded form under all conditions, but has the ability to do so under conditions that favor annealing of complementary nucleotide bases. Accordingly, the term "duplexed parvovirus vector" does not indicate that the vDNA is necessarily in duplexed or double-stranded form (e.g., there is base-pairing between the self-complementary strands) within the parvovirus capsid. Indeed, one skilled in the art will understand that the vDNA is likely not in a double-stranded form while packaged within the parvovirus capsid.

Expression of a heterologous nucleotide sequence (as described below) is preferably "enhanced" from the duplexed parvovirus vectors of the invention as compared with the comparable parvovirus (e.g., rAAV) vector. Preferably, gene expression may be detected from the duplexed parvovirus vector substantially more rapidly than from the comparable monomeric parvovirus vector. For example, gene expression may be detected in less than about 2 weeks, preferably less than about one week, more preferably less than about 72 hours, still more preferably less than about 48 hours, and still more preferably less than about 24 hours after administration of the duplexed parvovirus vector. Gene expression may be detected by any method known in the art, e.g., by detecting transcription, translation, or biological activity or a phenotypic effect resulting from expression of a heterologous nucleotide sequence (e.g., blood clotting time).

Alternatively, gene expression from the duplexed parvovirus vector may be "enhanced" in that higher levels of gene expression (as defined in the preceding paragraph) are detected as compared with the comparable monomeric parvovirus vector (e.g., rAAV vector). Comparisons may be made in the level of gene expression at the same time point after administration of virus. Alternatively, comparisons may be made between the maximum level of gene expression achieved with each vector.

The duplexed parvovirus vectors of the invention may advantageously have improved transduction unit (tu) to particle ratios as compared with conventional parvovirus vectors. Accordingly, the present invention also encompasses novel parvovirus vector compositions having an improved tu/particle ratio over compositions of conventional parvovirus vectors (e.g., rAAV vectors). Preferably, the tu/particle ratio is less than about 50:1, less than about 20:1, less than about 15:1, less than about 10:1, less than about 8:1, less than about 7:1, less than about 6:1, less than about 5:1, less than about 4:1, or lower. There is no particular lower limit to the tu/particle ratio. Typically, the tu/particle ratio will be greater than about 1:1, 2:1, 3:1 or 4:1.

The term "template" or "substrate" is typically used herein to refer to a polynucleotide sequence that may be replicated to produce the duplexed parvovirus vDNA of the invention. For the purpose of vector production, the template will typically be embedded within a larger nucleotide sequence or construct, including but not limited to a plasmid, naked DNA vector, bacterial artificial chromosome (BAC), yeast artificial chromosome (YAC) or a viral vector (e.g., adenovirus, herpesvirus, Epstein-Barr Virus, AAV, baculoviral, retroviral vectors, and the like). Alternatively, the template may be stably incorporated into the chromosome of a packaging cell.

As used herein, the term "polypeptide" encompasses both peptides and proteins, unless indicated otherwise.

As used herein, "transduction" or "infection" of a cell by AAV means that the AAV enters the cell to establish a latent or active (i.e., lytic) infection, respectively. See, e.g., BERNARD N. FIELDS et al., VIROLOGY, volume 2, chapter 69 (3d ed., Lippincott-Raven Publishers). In embodiments of the invention in which a rAAV vector is introduced into a cell for the purpose of delivering a nucleotide sequence to the cell, it is preferred that the AAV integrates into the genome and establishes a latent infection.

Duplexed Parvovirus Vectors.

The present invention is based, in part, on the discovery that "duplexed" DNA parvovirus vectors (as described above) can be advantageously employed for gene delivery. Furthermore, the present investigations have demonstrated that these duplexed parvovirus vectors may be more efficient than AAV vectors, e.g., improved transducing to particle ratios, more rapid transgene expression, a higher level of transgene expression, and/or more persistent transgene expression. The inventors have further demonstrated that the duplexed parvovirus vectors of the invention may be used for gene delivery to host cells that are typically refractory to AAV transduction. Thus, these duplexed parvovirus vectors have a different (e.g., broader) host range than do AAV vectors.

The duplexed parvovirus vectors disclosed herein are dimeric self-complementary (sc) polynucleotides (typically, DNA) packaged within a viral capsid, preferably a parvovirus capsid, more preferably, an AAV capsid. In some respects, the viral genome that is packaged within the capsid is essentially a "trapped" replication intermediate that cannot be resolved to produce the plus and minus polarity parvovirus DNA strands. Accordingly, the duplexed parvovirus vectors of the invention appear to circumvent the need for host cell mediated synthesis of complementary DNA inherent in conventional recombinant AAV (rAAV) vectors, thereby addressing one of the limitations of rAAV vectors.

This result is accomplished by allowing the virus to package essentially dimeric inverted repeats of the single-stranded parvovirus (e.g., AAV) vector genome such that both strands, joined at one end, are contained within a single infectious capsid. Upon release from the capsid, the complementary sequences re-anneal to form transcriptionally active double-stranded DNA within the target cell.

The duplexed parvovirus vectors disclosed herein are fundamentally different from conventional parvovirus (e.g., rAAV) vectors, and from the parent parvovirus (e.g., AAV), in that the vDNA may form a double-stranded hairpin structure due to intrastrand base pairing, and that both DNA strands are encapsidated. Thus, the duplexed parvovirus vector is functionally similar to double-stranded DNA virus vectors rather than the parvovirus from which it was derived. This feature addresses a previously recognized shortcoming of rAAV mediated gene transfer, which is the limited propensity of the desired target cell to synthesize complementary DNA to the single-stranded genome normally encapsidated by the Parvoviridae.

The viral capsid may be from any parvovirus, either an autonomous parvovirus or dependovirus, as described above. Preferably, the viral capsid is an AAV capsid (e.g., AAV1, AAV2, AAV3, AAV4, AAV5 or AAV6 capsid). In general, the AAV1 capsid, AAV5 capsid, and AAV3 capsid are preferred. The choice of parvovirus capsid may be based on a number of considerations as known in the art, e.g., the target cell type, the desired level of expression, the nature of the heterologous nucleotide sequence to be expressed, issues related to viral production, and the like. For example, the AAV1 capsid may be advantageously employed for skeletal muscle, liver and cells of the central nervous system (e.g., brain); AAV5 for cells in the airway and lung; AAV3 for bone marrow cells; and AAV4 for particular cells in the brain (e.g., appendable cells).

The parvovirus particle may be a "hybrid" particle in which the viral TRs and viral capsid are from different parvoviruses. Preferably, the viral TRs and capsid are from different serotypes of AAV (e.g., as described in international patent publication WO 00/28004, U.S. provisional application No. 60/248,920; and Chao et al., (2000) *Molecular Therapy* 2:619; the disclosures of which are incorporated herein in their entireties. Likewise, the parvovirus may have a "chimeric" capsid (e.g., containing sequences from different parvoviruses) or a "targeted" capsid (e.g., a directed tropism) as described in these publications.

As used herein, a "duplexed parvovirus particle" encompasses hybrid, chimeric and targeted virus particles. Preferably, the duplexed parvovirus particle has an AAV capsid, which may further by a chimeric or targeted capsid, as described above.

A duplexed parvovirus vector according to the invention may be produced by any suitable method. Preferably, the template for producing the vDNA is one that preferentially gives rise to a duplexed, rather than monomeric vDNA (i.e., the majority of vDNA produced are duplexed) which has the capacity to form a double-stranded vDNA. Preferably, at least about 50%, 60%, 70%, 80%, 90%, 95%, 98%, 99% or more of the replication products from the template are duplexed.

In one particular embodiment, the template is a DNA molecule comprising one or more terminal repeat (TR) sequences. The template also comprises a modified TR that cannot be resolved (i.e., nicked) by the parvovirus Rep proteins. During replication, the inability of Rep protein to resolve the modified TR will result in a stable intermediate with the two "monomers" covalently attached by the non-resolvable TR. This "duplexed" molecule may be packaged within the parvovirus (AAV) capsid to produce a novel duplexed parvovirus vector.

While not wishing to be held to any particular theory of the invention, it is likely that the virion genome is retained in a single-stranded form while packaged within the viral capsid. Upon release from the capsid during viral infection, it appears that the dimeric molecule "snaps back" or anneals to form a double-stranded molecule by intra-strand basepairing, with the non-resolvable TR sequence forming a covalently-closed hairpin structure at one end. This double-stranded vDNA obviates host cell mediated second-strand synthesis, which has been postulated to be a rate-limiting step for AAV transduction.

In preferred embodiments, the template further comprises a heterologous nucleotide sequence(s) (as described below) to be packaged for delivery to a target cell. According to this particular embodiment, the heterologous nucleotide sequence is located between the viral TRs at either end of the substrate. In further preferred embodiments, the parvovirus (e.g., AAV) cap genes and parvovirus (e.g., AAV) rep genes are deleted from the template (and the vDNA produced therefrom). This configuration maximizes the size of the heterologous nucleic acid sequence(s) that can be carried by the parvovirus capsid.

In one particular embodiment, the template for producing the inventive duplexed parvovirus vectors contains at least one TR at the 5' and 3' ends, flanking a heterologous nucleotide sequence of interest (as described below). The TR at one end of the substrate is non-resolvable, i.e., it cannot be resolved (nicked) by Rep protein. During replication, the inability of Rep protein to resolve one of the TRs will result in a stable intermediate with the two "monomers" covalently attached by the non-functional (i.e., non-resolvable) TR. The heterologous nucleotide sequence may be in either orientation with respect to the non-resolvable TR.

The term "flanked" is not intended to indicate that the sequences are necessarily contiguous. For example, in the example in the previous paragraph, there may be intervening sequences between the heterologous nucleotide sequence and the TR. A sequence that is "flanked" by two other elements, indicates that one element is located 5' to the sequence and the other is located 3' to the sequence; however, there may be intervening sequences therebetween.

According to this embodiment, the template for producing the duplexed parvovirus vDNA of the invention is preferably about half of the size of the wild-type parvovirus genome (e.g., AAV) corresponding to the capsid into which the vDNA will be packaged. Alternatively, stated, the template is preferably from about 40% to about 55% of wt, more preferably from about 45% to about 52% of wt. Thus, the duplexed vDNA produced from this template will preferably have a total size that is approximately the size of the wild-type parvovirus genome (e.g., AAV) corresponding to the capsid into which the vDNA will be packaged, e.g., from about 80% to about 105% of wt. In the case of AAV, it is well-known in the art that the AAV capsid disfavors packaging of vDNA that substantially deviate in size from the wt AAV genome. In the case of an AAV capsid, the duplexed vDNA is preferably approximately 5.2 kb in size or less. In other embodiments, the duplexed vDNA is preferably greater than about 3.6, 3.8, 4.0, 4.2, or 4.4 kb in length and/or less than about 5.4, 5.2, 5.0 or 4.8 kb in length.

Alternatively stated, the heterologous nucleotide sequence(s) will typically be less than about 2.5 kb in length (more preferably less than about 2.4 kb, still more preferably less than about 2.2 kb in length, yet more preferably less than about 2.1 kb in length) to facilitate packaging of the duplexed template by the parvovirus (e.g., AAV) capsid.

In another particular embodiment, the template itself is duplexed, i.e., is a dimeric self-complementary molecule. According to this embodiment, the template comprises a resolvable TR at either end. The template further comprises a centrally-located non-resolvable TR (as described above). In other words, each half of the template on either side of the non-resolvable TR is approximately the same length. Each half of the template (i.e., between the resolvable and non-resolvable TR) comprises one or more heterologous nucleotide sequence(s) of interest. The heterologous nucleotide sequence(s) in each half of the molecule is flanked by a resolvable TR and the central non-resolvable TR.

The sequences in either half of the template are substantially complementary (i.e., at least about 90%, 95%, 98%, 99% nucleotide sequence complementarity or more), so that the replication products from the template may form double-stranded molecules due to base-pairing between the complementary sequences. In other words, the template is essentially an inverted repeat with the two halves joined by the non-resolvable TR.

Preferably, the heterologous nucleotide sequence(s) in each half of the template are essentially completely self-complementary (i.e., contains an insignificant number of mismatched bases, or even no mismatched bases). It is also preferred that the two halves of the nucleotide sequence are essentially completely self-complementary.

According to this embodiment, the template (and the vDNA produced therefrom) is preferably approximately the same size as the wt genome naturally encapsulated by the parvovirus capsid (e.g., AAV), i.e., to facilitate efficient packaging into the parvovirus capsid. For example, in the case of an AAV capsid, the template is preferably approximately the size of the wt AAV genome. In particular embodiments, the template is approximately 5.2 kb in size or less. In other embodiments, the template is preferably greater than about 3.6, 3.8, 4.0, 4.2, or 4.4 kb in length and/or less than about 5.4, 5.2, 5.0 or 4.8 kb in length. As an alternative statement, the template is preferably in the range of 80% to 105% of the wildtype parvovirus genome (e.g., AAV).

The TR(s) (resolvable and non-resolvable) are preferably AAV sequences, with serotypes 1, 2, 3, 4, 5 and 6 being preferred. The term "terminal repeat" includes synthetic sequences that function as an AAV inverted terminal repeat, such as the "double-D sequence" as described in U.S. Pat. No. 5,478,745 to Samulski et al., the disclosure of which is incorporated in its entirety herein by reference. Resolvable AAV TRs according to the present invention need not have a wild-type TR sequence (e.g., a wild-type sequence may be altered by insertion, deletion, truncation or missense mutations), as long as the TR mediates the desired functions, e.g., virus packaging, integration, and/or provirus rescue, and the like. Typically, but not necessarily, the TRs are from the same parvovirus, e.g., both TR sequences are from AAV2.

Those skilled in the art will appreciate that the viral Rep protein(s) used for producing the inventive duplexed vectors are selected with consideration for the source of the viral TRs. For example, the AAV5 TR interacts more efficiently with the AAV5 Rep protein.

The genomic sequences of the various autonomous parvoviruses and the different serotypes of AAV, as well as the sequences of the TRs, capsid subunits, and Rep proteins are known in the art. Such sequences may be found in the literature or in public databases such as GenBank. See, e.g., GenBank Accession Numbers NC 002077, NC 001863, NC 001862, NC 001829, NC 001729, NC 001701, NC 001510, NC 001401, AF063497, U89790, AF043303, AF028705, AF028704, J02275, J01901, J02275, X01457, AF288061, AH009962, AY028226, AY028223, NC 001358, NC 001540; the disclosures of which are incorporated herein in their entirety. See also, e.g., Chiorini et al., (1999) *J. Virology* 73:1309; Xiao et al., (1999) *J. Virology* 73:3994; Muramatsu et al., (1996) *Virology* 221:208; international patent publications WO 00/28061, WO 99/61601, WO 98/11244; U.S. Pat. No. 6,156,303; the disclosures of which are incorporated herein in their entirety. An early description of the AAV1, AAV2 and AAV3 TR sequences is provided by Xiao, X., (1996), "Characterization of Adeno-associated virus (AAV) DNA replication and integration," Ph.D. Dissertation, University of Pittsburgh, Pittsburgh, Pa. (incorporated herein it its entirety).

Figure 5:
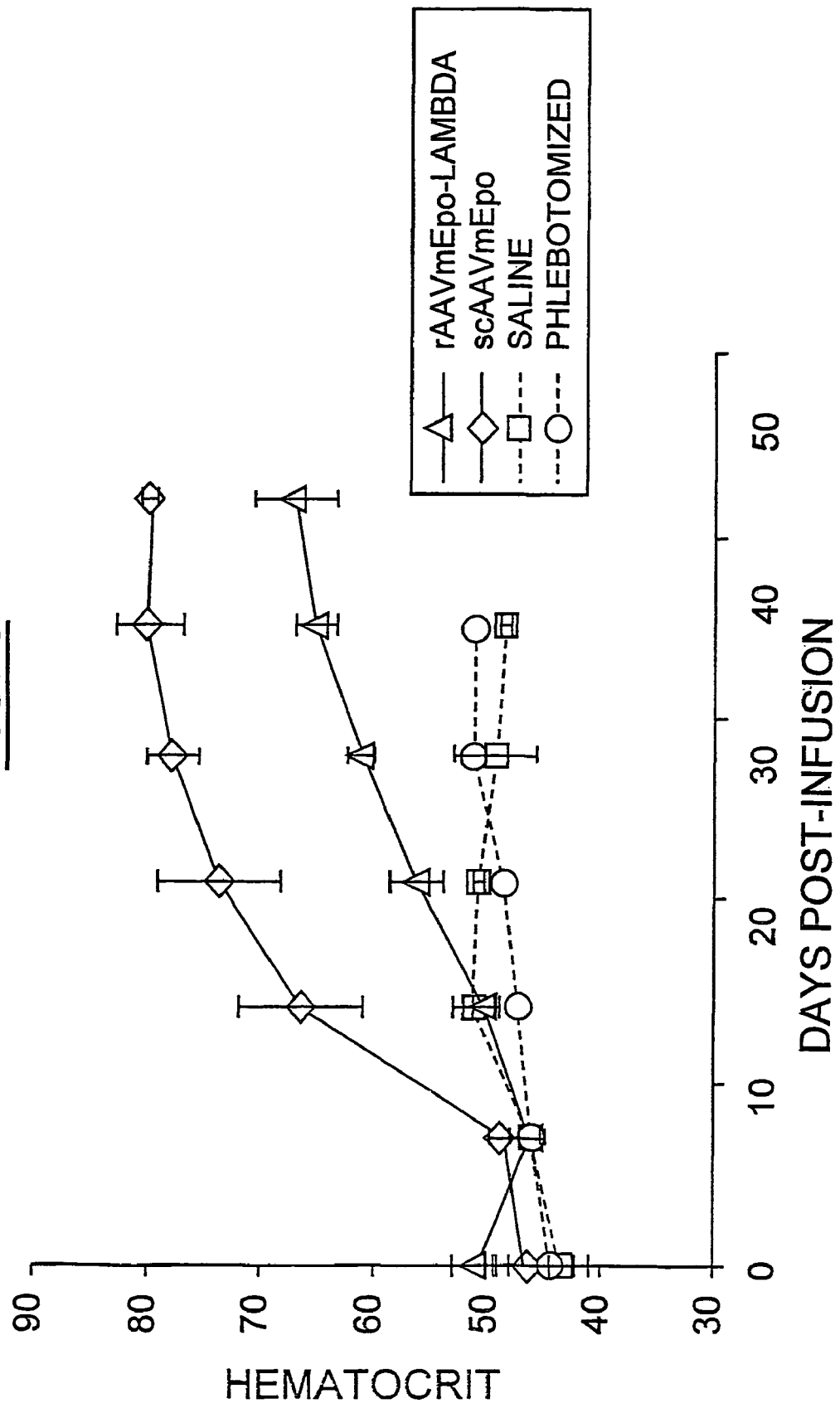
FIG. 5. In vivo transduction of mouse liver tissue with duplexed or single-stranded rAAV vectors. Ten week old Balb-c ByJ mice were infused with 2×10$^{10}$ particles of either scAAV-CMV-mEpo, ♦, (n=4), or full-length single-stranded rAAV-CMV-mEpoλ, ▲, (n=5), in 200 µl normal saline by portal vein injection. One group of control mice was infused with normal saline, □, (n=4), and a single mouse, ○, was phlebotomized at the same 7-day intervals without prior surgery. Blood hematocrit was used as a functional measure of mEpo expression.

The non-resolvable TR may be produced by any method known in the art. For example, insertion into the TR will displace the nicking site (i.e., trs) and result in a non-resolvable TR. The designation of the various regions or elements within the TR are known in the art. An illustration of the regions within the AAV TR is provided in FIG. 6 (see also, BERNARD N. FIELDS et al., VIROLOGY, volume 2, chapter 69, FIG. 5, 3d ed., Lippincott-Raven Publishers). The insertion is preferably made into the sequence of the terminal resolution site (trs). Alternatively, the insertion may be made at a site between the Rep Binding Element (RBE) within the A element and the trs, which is adjacent to the D element (see FIG. 6). The core sequence of the AAV trs site is known in the art and has been described by Snyder et al., (1990) *Cell* 60:105; Snyder et al., (1993) *J. Virology* 67:6096; Brister & Muzyczka, (2000) *J. Virology* 74:7762; Brister & Muzyczka, (1999) *J. Virology* 73:9325 (the disclosures of which are hereby incorporated by reference in their entireties). For example, Brister & Muzyczka, (1999) *J. Virology* 73:9325 describes a core trs sequence of 3'-CCGGT/TG-5' adjacent to the D element. Snyder et al., (1993) *J. Virology* 67:6096 identified the minimum trs sequence as 3'-GGT/TGA-5', which substantially overlaps the sequence identified by Brister & Muzyczka.

Preferably, the insertion is in the region of the trs site. The insertion may be of any suitable length that will reduce or substantially eliminate (e.g., by 60%, 70%, 80%. 90%, 95% or greater) resolution of the TR. Preferably, the insertion is at least about 3, 4, 5, 6, 10, 15, 20 or 30 nucleotides or more. There are no particular upper limits to the size of the inserted sequence, as long as suitable levels of viral replication and packaging are achieved (e.g., the insertion can be as long as 50, 100, 200 or 500 nucleotides or longer).

In another preferred embodiment, the TR may be rendered non-resolvable by deletion of the trs site. The deletions may extend 1, 3, 5, 8, 10, 15, 20, 30 nucleotides or more beyond the trs site, as long as the template retains the desired functions. In addition to the trs site, some or all of the D element may be deleted. Deletions may further extend into the A element, however those skilled in the art will appreciate that it may be advantageous to retain the RBE in the A element, e.g., to facilitate efficient packaging. Deletions into the A element may be 2, 3, 4, 5, 8, 10, or 15 nucleotides in length or more, as long as the non-resolvable TR retains any other desired functions. It is further preferred that some or all of the parvovirus (e.g., AAV) sequences going beyond the D element outside the TR sequence (e.g., to the right of the D element in FIG. 6) be deleted to prevent gene conversion to correct the altered TR.

As still a further alternative, the sequence at the nicking site may be mutated so that resolution by Rep protein is reduced or substantially eliminated. For example, A and/or C bases may be substituted for G and/or T bases at or near the nicking site. The effects of substitutions at the terminal resolution site on Rep cleavage have been described by Brister & Muzyczka, (1999) *J. Virology* 73:9325 (the disclosure of which is hereby incorporated by reference). As a further alternative, nucleotide substitutions in the regions surrounding the nicking site, which have been postulated to form a stem-loop structure, may also be used to reduce Rep cleavage at the terminal resolution site (Id.).

Those skilled in the art will appreciate that the alterations in the non-resolvable TR may be selected so as to maintain desired functions, if any, of the altered TR (e.g., packaging, Rep recognition, site-specific integration, and the like).

In more preferred embodiments, the TR will be resistant to the process of gene conversion as described by Samulski et al., (1983) *Cell* 33:135. Gene conversion at the non-resolvable TR will restore the trs site, which will generate a resolvable TR and result in an increase in the frequency of monomeric replication products. Gene conversion results by homologous recombination between the resolvable TR and the altered TR.

One strategy to reduce gene conversion is to produce virus using a cell line (preferably, mammalian) that is defective for DNA repair, as known in the art, as these cell lines will be impaired in their ability to correct the mutations introduced into the viral template.

Alternatively, templates that have a substantially reduced rate of gene conversion can be generated by introducing a region of non-homology into the non-resolvable TR. Non-homology in the region surrounding the trs element between the non-resolvable TR and the unaltered TR on the template will reduce or even substantially eliminate gene conversion.

Any suitable insertion or deletion may be introduced into the non-resolvable TR to generate a region of non-homology, as long as gene conversion is reduced or substantially eliminated. Strategies that employ deletions to create non-homology are preferred. It is further preferred that the deletion does not unduly impair replication and packaging of the template. In the case of a deletion, the same deletion may suffice to impair resolution of the trs site as well as to reduce gene conversion.

As a further alternative, gene conversion may be reduced by insertions into the non-resolvable TR or, alternatively, into the A element between the RBE and the trs site. The insertion is typically at least about 3, 4, 5, 6, 10, 15, 20 or 30 nucleotides or more nucleotides in length. There is no particular upper limit to the size of the inserted sequence, which may be as long as 50, 100, 200 or 500 nucleotides or longer, however, it is preferred that the insertion does not unduly impair replication and packaging of the template.

In alternative embodiments, the non-resolvable TR may be a naturally-occurring TR (or altered form thereof) that is non-resolvable under the conditions used. For example, the non-resolvable TR may not be recognized by the Rep proteins used to produce the vDNA from the template. To illustrate, the non-resolvable TR may be an autonomous parvovirus sequence that is not recognized by AAV Rep proteins. As an another illustrative example, the resolvable TR and Rep proteins may be from one AAV serotype (e.g., AAV2), and the non-resolvable TR will be from another AAV serotype (e.g., AAV5) that is not recognized by the AAV2 Rep proteins.

As a yet further alternative, the non-resolvable sequence may be any inverted repeat sequence that forms a hairpin structure and cannot be cleaved by the Rep proteins.

As still a further alternative, a half-genome size template may be used to produce a parvovirus particle carrying a duplexed vDNA, produced from a half-genome sized template, as described in the Examples herein and by Hirata & Russell, (2000) *J. Virology* 74:4612. This report describes packaging of paired monomers and transient RF intermediates when AAV genomes were reduced to less than half-size of the wtAAV genome (<2.5 kb). These investigators found that monomeric genomes were the preferred substrate for gene correction by homologous recombination, and that duplexed genomes functioned less well than did monomeric genomes in this assay. This report did not investigate or suggest the use of duplexed genomes as vectors for gene delivery.

Preferably, according to this embodiment, the template will be approximately one-half of the size of the vDNA that can be packaged by the parvovirus capsid. For example, for an AAV capsid, the template is preferably approximately one-half of the wt AAV genome in length, as described above.

The template (as described above) is replicated to produce a duplexed vector genome (vDNA) of the invention, which is capable of forming a double-stranded DNA under appropriate conditions. The duplexed molecule is substantially self-complementary so as to be capable of forming a double-stranded viral DNA (i.e., at least 90%, 95%, 98%, 99% nucleotide sequence complementarity or more). Base-pairing between individual nucleotide bases or polynucleotide sequences is well-understood in the art. Preferably, the duplexed parvovirus viral DNA is essentially completely self-complementary (i.e., contains no or an insignificant number of mis-matched bases). In particular, it is preferred that the heterologous nucleotide sequence(s) (e.g., the sequences to be transcribed by the cell) are essentially completely self-complementary.

In general, the duplexed parvoviruses may contain non-complementarity to the extent that expression of the heterologous nucleotide sequence(s) from the duplexed parvovirus vector is more efficient than from a corresponding monomeric vector.

The duplexed parvoviruses of the present invention provide the host cell with a double-stranded molecule that addresses one of the drawbacks of rAAV vectors, i.e., the need for the host cell to convert the single-stranded rAAV vDNA into a double-stranded DNA. The presence of any substantial regions of non-complementarity within the virion DNA, in particular, within the heterologous nucleotide sequence(s) will likely be recognized by the host cell, and will result in DNA repair mechanisms being recruited to correct the mis-matched bases, thereby counteracting the advantageous characteristics of the duplexed parvovirus vectors, e.g., the inventive vectors reduce or eliminate the need for the host cell to process the viral template.

Production of Duplexed Parvovirus Vectors.

In general, methods of producing AAV vectors are applicable to producing the duplexed parvovirus vectors of the invention; the primary difference between the methods is the structure of the template or substrate to be packaged. To produce a duplexed parvovirus vector according to the present invention, a template as described above will be used to produce the encapsidated viral genome.

The template described above is preferably a DNA substrate and may be provided in any form known in the art, including but not limited to a plasmid, naked DNA vector, bacterial artificial chromosome (BAC), yeast artificial chromosome (YAC) or a viral vector (e.g., adenovirus, herpesvirus, Epstein-Barr Virus, AAV, baculoviral, retroviral vectors, and the like). Alternatively, the template may be stably incorporated into the genome of a packaging cell.

In one particular embodiment, the inventive parvovirus vectors may carry duplexed half-genome sized monomeric vDNA as described in the Examples herein. This means of providing cells with a duplexed parvovirus (e.g., AAV) virion DNA takes advantage of the rolling-hairpin mode of replication in which monomeric vDNA is generated from dimeric inverted repeat intermediates (Cavalier-Smith et al., (1974) *Nature* 250:467; Straus et al., (1976) *Proc. Nat. Acad. Sci. USA* 73:742). When the genome is sufficiently small, the dimeric inverted repeats themselves can be encapsidated into the virion. This approach will generate a mixed population of monomeric and dimeric molecules. The duplexed parvovirus vectors may be isolated by known techniques, e.g., separation over a cesium chloride density gradient.

Duplexed parvovirus particles according to the invention may be produced by any method known in the art, e.g., by introducing the template to be replicated and packaged into a permissive or packaging cell, as those terms are understood in the art (e.g., a "permissive" cell can be infected or transduced by the virus; a "packaging" cell is a stably transformed cell providing helper functions).

In one embodiment, a method is provided for producing a duplexed parvovirus particle, comprising: providing to a cell permissive for parvovirus replication (a) a nucleotide sequence encoding a template for producing vector genome of the invention (as described in detail above); (b) nucleotide sequences sufficient for replication of the template to produce a vector genome; (c) nucleotide sequences sufficient to package the vector genome into a parvovirus capsid, under conditions sufficient for replication and packaging of the vector genome into the parvovirus capsid, whereby duplexed parvovirus particles comprising the vector genome encapsidated within the parvovirus capsid are produced in the cell. Preferably, the parvovirus replication and/or capsid coding sequences are AAV sequences.

Any method of introducing the nucleotide sequence carrying the template into a cellular host for replication and packaging may be employed, including but not limited to, electroporation, calcium phosphate precipitation, microinjection, cationic or anionic liposomes, and liposomes in combination with a nuclear localization signal. In embodiments wherein the template is provided by a virus vector, standard methods for producing viral infection may be used.

Any suitable permissive or packaging cell known in the art may be employed to produce the duplexed vectors. Mammalian cells are preferred. Also preferred are trans-complementing packaging cell lines that provide functions deleted from a replication-defective helper virus, e.g., 293 cells or other E1a trans-complementing cells. Also preferred are mammalian cells or cell lines that are defective for DNA repair as known in the art, as these cell lines will be impaired in their ability to correct the mutations introduced into the viral template.

The template may contain some or all of the parvovirus (e.g., AAV) cap and rep genes. Preferably, however, some or all of the cap and rep functions are provided in trans by introducing a packaging vector(s) encoding the capsid and/or Rep proteins into the cell. Most preferably, the template does not encode the capsid or Rep proteins. Alternatively, a packaging cell line is used that is stably transformed to express the cap and/or rep genes (see, e.g., Gao et al., (1998) *Human Gene Therapy* 9:2353; Inoue et al., (1998) *J. Virol.* 72:7024; U.S. Pat. No. 5,837,484; WO 98/27207; U.S. Pat. No. 5,658,785; WO 96/17947).

In addition, helper virus functions are preferably provided for the vector to propagate new virus particles. Both adenovirus and herpes simplex virus may serve as helper viruses for AAV. See, e.g., BERNARD N. FIELDS et al., VIROLOGY, volume 2, chapter 69 (3d ed., Lippincott-Raven Publishers). Exemplary helper viruses include, but are not limited to, Herpes simplex (HSV) varicella zoster, cytomegalovirus, and Epstein-Barr virus. The multiplicity of infection (MOI) and the duration of the infection will depend on the type of virus used and the packaging cell line employed. Any suitable helper vector may be employed. Preferably, the helper vector(s) is a plasmid, for example, as described by Xiao et al., (1998) *J. Virology* 72:2224. The vector can be introduced into the packaging cell by any suitable method known in the art, as described above.

In one method, the inventive duplexed parvovirus vectors may be produced by co-transfection of a rep/cap vector encoding AAV packaging functions and the template encoding the AAV vDNA into human cells infected with adenovirus (Samulski et al., (1989) *J. Virology* 63:3822). Under optimized conditions, this procedure can yield up to $10^9$ infectious units of virus particles per ml. One drawback of this method, however, is that it results in the co-production of contaminating wild-type adenovirus. Since several adenovirus proteins (e.g., fiber, hexon, etc.) are known to produce a cytotoxic T-lymphocyte (CTL) immune response in humans (Yang and Wilson, (1995) *J. Immunol.* 155:2564; Yang et al., (1995) *J. Virology* 69:2004; Yang et al., (1994) *Proc. Nat. Acad. Sci. USA* 91:4407), this represents a significant drawback when using these rAAV preparations (Monahan et al., (1998) *Gene Therapy* 5:40).

Vector stocks free of contaminating helper virus may be obtained by any method known in the art. For example, duplexed virus and helper virus may be readily differentiated based on size. The duplexed virus may also be separated away from helper virus based on affinity for a heparin substrate (Zolotukhin et al. (1999) *Gene Therapy* 6:973). Preferably, deleted replication-defective helper viruses are used so that any contaminating helper virus is not replication competent. As a further alternative, an adenovirus helper lacking late gene expression may be employed, as only adenovirus early gene expression is required to mediate packaging of the duplexed virus. Adenovirus mutants defective for late gene expression are known in the art (e.g., ts100K and ts149 adenovirus mutants).

A preferred method for providing helper functions employs a non-infectious adenovirus miniplasmid that carries all of the helper genes required for efficient AAV production (Ferrari et al., (1997) *Nature Med.* 3:1295; Xiao et al., (1998) *J. Virology* 72:2224). The rAAV titers obtained with adenovirus miniplasmids are forty-fold higher than those obtained with conventional methods of wild-type adenovirus infection (Xiao et al., (1998) *J. Virology* 72:2224). This approach obviates the need to perform co-transfections with adenovirus (Holscher et al., (1994), *J. Virology* 68:7169; Clark et al., (1995) *Hum. Gene Ther.* 6:1329; Trempe and Yang, (1993), in, *Fifth Parvovirus Workshop*, Crystal River, Fla.).

Other methods of producing rAAV stocks have been described, including but not limited to, methods that split the rep and cap genes onto separate expression cassettes to prevent the generation of replication-competent AAV (see, e.g., Allen et al., (1997) *J. Virol.* 71:6816), methods employing packaging cell lines (see, e.g., Gao et al., (1998) *Human Gene Therapy* 9:2353; Inoue et al., (1998) *J. Virol.* 72:7024; U.S. Pat. No. 5,837,484; WO 98/27207; U.S. Pat. No. 5,658,785; WO 96/17947), and other helper virus free systems (see, e.g., U.S. Pat. No. 5,945,335 to Colosi).

Herpesvirus may also be used as a helper virus in AAV packaging methods. Hybrid herpesviruses encoding the AAV Rep protein(s) may advantageously facilitate for more scalable AAV vector production schemes. A hybrid herpes simples virus type I (HSV-1) vector expressing the AAV-2 rep and cap genes has been described (Conway et al., (1999) *Gene Therapy* 6:986 and WO 00/17377, the disclosures of which are incorporated herein in their entireties).

In sum, the viral template to be replicated and packaged, parvovirus cap genes, appropriate parvovirus rep genes, and (preferably) helper functions are provided to a cell (e.g., a permissive or packaging cell) to produce parvovirus particles carrying the duplexed genome (i.e., the genome is capable of forming a "snap back" or self-complementary DNA after viral uncoating). The combined expression of the rep and cap genes encoded by the template and/or the packaging vector(s) and/or the stably transformed packaging cell results in the production of a parvovirus particle in which a parvovirus capsid packages a duplexed parvovirus genome according to the invention. The duplexed parvovirus particles are allowed to assemble within the cell, and may then be recovered by any method known by those of skill in the art.

Alternatively, in vitro packaging approaches, as are known in the art, may also be used to produce the dimeric vDNA templates described herein. To illustrate, the duplexed vDNA sequence may be amplified in bacteria using single-stranded M13 phage. The resolvable TRs at each end of the vDNA carried by the M13 will anneal to form a double-stranded sequence, which may be cleaved with a suitable restriction enzyme to excise the dimeric vDNA from the M13 backbone. As yet a further alternative, PCR or other suitable amplification techniques may be used to amplify the duplexed vDNA sequence from a dimeric self-complementary template, as described above.

The reagents and methods disclosed herein may be employed to produce high-titer stocks of the inventive parvovirus vectors, preferably at essentially wild-type titers. It is also preferred that the parvovirus stock has a titer of at least about $10^5$ transducing units (tu)/ml, more preferably at least about $10^6$ tu/ml, more preferably at least about $10^7$ tu/ml, yet more preferably at least about $10^8$ tu/ml, yet more preferably at least about $10^9$ tu/ml, still yet more preferably at least about $10^{10}$ tu/ml, still more preferably at least about $10^{11}$ tu/ml, or more.

Alternatively stated, the parvovirus stock preferably has a titer of at least about 1 tu/cell, more preferably at least about 5 tu/cell, still more preferably at least about 20 tu/cell, yet more preferably at least about 50 tu/cell, still more preferably at least about 100 tu/cell, more preferably still at least about 250 tu/cell, most preferably at least about 500 tu/cell, or even more.

Further, the duplexed parvovirus vectors of the invention, may have an improved transducing unit (tu)/particle ratio over conventional parvovirus vectors. Preferably, the tu/particle ratio is less than about 50:1, less than about 20:1, less than about 15:1, less than about 10:1, less than about 8:1, less than about 7:1, less than about 6:1, less than about 5:1, less than about 4:1, or lower. There is no particular lower limit to the tu/particle ratio. Typically, the tu/particle ratio will be greater than about 1:1, 2:1, 3:1 or 4:1.

Applications of the Present Invention.

A further aspect of the invention is a method of delivering a nucleotide sequence to a cell using the duplexed parvovirus vectors described herein. The vector may be delivered to a cell in vitro or to a subject in vivo by any suitable method known in the art. Alternatively, the vector may be delivered to a cell ex vivo, and the cell administered to a subject, as known in the art.

The present methods may be advantageously employed to provide more efficient transduction of target cells than wtAAV vectors. To illustrate, the duplexed parvovirus vectors may transduce at a higher rate than wt AAV vectors. Alternatively, or additionally, the duplexed parvovirus vectors may provide for a more rapid onset of transgene expression, a higher level of transgene expression, and/or a longer persistence of transgene expression than AAV vectors.

The inventive duplexed parvovirus vectors and methods may further find use in methods of administering a nucleotide sequence to a cell that is typically non-permissive for transduction by AAV, or is only inefficiently transduced by AAV. Exemplary cells include but are not limited to dendritic cells, particular types of cancer or tumor cells, astrocytes, and bone marrow stem cells. Moreover, the methods disclosed herein may be advantageously practiced with non-replicating or slowly-replicating cells that only inefficiently support second-strand AAV synthesis, such as the liver, central nervous system (e.g., brain), and particular populations of cells within muscle (e.g., fast-twitch fibers).

Accordingly, the duplexed parvovirus vectors disclosed herein may have a distinct target cell range (e.g., a broader range of target cells) as compared with rAAV vectors. While not wishing to be held to any particular theory of the invention, it appears that cells that are refractory to transduction by rAAV may be permissive for the inventive duplexed parvovirus vectors, which provide a double-stranded molecule to the host cell. Thus, the present invention finds use for delivering a nucleotide sequence to a cell that is non-permissive for conventional rAAV vectors or only poorly transduced by rAAV vectors because it cannot efficiently support second-strand synthesis of the viral DNA.

One of the characteristics of wtAAV vectors is the protracted lag period before high level transgene expression is observed. The duplexed parvovirus vectors disclosed herein may provide a more rapid and aggressive gene delivery system than wtAAV vectors because they obviate the step of complementary strand synthesis.

Accordingly, the inventive duplexed parvovirus vectors find use in methods of treating cancer or tumors, e.g., by delivery of anti-cancer agents or cancer antigens. In particular embodiments, the inventive methods are used to administer anti-cancer agents or cancer antigens to prevent metastasis, e.g., following surgical removal of a primary tumor.

The inventive methods and duplexed parvovirus vectors may also advantageously be used in the treatment of individuals with metabolic disorders (e.g., ornithine transcarbamylase deficiency). Such disorders typically require a relatively rapid onset of expression of a therapeutic polypeptide by the gene delivery vector. As still a further alternative, the inventive vectors may be administered to provide agents that improve transplant survivability (e.g., superoxide dismutase) or combat sepsis.

Moreover, the inventors have found that dendritic cells (DC), which are refractory to wtAAV vectors (Jooss et al., (1998) 72:4212), are permissive for the duplexed parvovirus vectors disclosed herein. Accordingly, as yet a further aspect, the present invention provides methods of delivering a nucleotide sequence to DC, e.g., to induce an immune response to a polypeptide encoded by the nucleotide sequence. Preferably, the nucleotide sequence encodes an antigen from an infectious agent or a cancer antigen.

As still a further aspect, the present invention may be employed to deliver a heterologous nucleotide sequence in situations in which it is desirable to regulate the level of transgene expression (e.g., transgenes encoding hormones or growth factors, as described below). The more rapid onset of transgene expression by the duplexed parvovirus vectors disclosed herein make these gene delivery vehicles more amenable to such treatment regimes than are rAAV vectors.

Any heterologous nucleotide sequence(s) (as defined above) may be delivered according to the present invention. Nucleic acids of interest include nucleic acids encoding polypeptides, preferably therapeutic (e.g., for medical or veterinary uses) or immunogenic (e.g., for vaccines) polypeptides.

A "therapeutic polypeptide" is a polypeptide that may alleviate or reduce symptoms that result from an absence or defect in a protein in a cell or subject. Alternatively, a "therapeutic polypeptide" is one that otherwise confers a benefit to a subject, e.g., anti-cancer effects or improvement in transplant survivability.

Preferably, the heterologous nucleotide sequence or sequences will be less than about 2.5 kb in length (more preferably less than about 2.4 kb, still more preferably less than about 2.2 kb, yet more preferably less than about 2.0 kb in length) to facilitate packaging of the duplexed template by the parvovirus (e.g., AAV) capsid. Exemplary nucleotide sequences encode Factor IX, Factor X, lysosomal enzymes (e.g., hexosaminidase A, associated with Tay-Sachs disease, or iduronate sulfatase, associated with Hunter Syndrome/MPS II), erythropoietin, angiostatin, endostatin, superoxide dismutase, globin, leptin, catalase, tyrosine hydroxylase, as well as cytokines (e.g., α-interferon, β-interferon, interferon-γ, interleukin-2, interleukin-4, interleukin 12, granulocyte-macrophage colony stimulating factor, lymphotoxin, and the like), peptide growth factors and hormones (e.g., somatotropin, insulin, insulin-like growth factors 1 and 2, platelet derived growth factor, epidermal growth factor, fibroblast growth factor, nerve growth factor, neurotrophic factor-3 and -4, brain-derived neurotrophic factor, glial derived growth factor, transforming growth factor-α and -β, and the like), receptors (e.g., tumor necrosis factor receptor). In other exemplary embodiments, the heterologous nucleotide sequence encodes a monoclonal antibodies, preferably a single-chained monoclonal antibody or a monoclonal antibody directed against a cancer or tumor antigen (e.g., HER2/neu, and as described below). Other illustrative heterologous nucleotide sequences encode suicide gene products (thymidine kinase, cytosine deaminase, diphtheria toxin, cytochrome P450, deoxycytidine kinase, and tumor necrosis factor), proteins conferring resistance to a drug used in cancer therapy, and tumor suppressor gene products.

As a further alternative, the heterologous nucleic acid sequence may encode a reporter polypeptide (e.g., an enzyme such as Green Fluorescent Protein, alkaline phosphatase).

Alternatively, in particular embodiments of the invention, the nucleic acid of interest may encode an antisense nucleic acid, a ribozyme (e.g., as described in U.S. Pat. No. 5,877, 022), RNAs that effect spliceosome-mediated trans-splicing (see, Puttaraju et al., (1999) *Nature Biotech.* 17:246; U.S. Pat. Nos. 6,013,487; 6,083,702), interfering RNAs (RNAi) that mediate gene silencing (see, Sharp et al., (2000) *Science* 287:2431) or other non-translated RNAs, such as "guide" RNAs (Gorman et al., (1998) *Proc. Nat. Acad. Sci. USA* 95:4929; U.S. Pat. No. 5,869,248 to Yuan et al.), and the like.

The parvovirus vector may also encode a heterologous nucleotide sequence that shares homology with and recombines with a locus on the host chromosome. This approach may be utilized to correct a genetic defect in the host cell.

The present invention may also be used to express an immunogenic polypeptide in a subject, e.g., for vaccination. The nucleic acid may encode any immunogen of interest known in the art including, but are not limited to, immunogens from human immunodeficiency virus, influenza virus, gag proteins, tumor antigens, cancer antigens, bacterial antigens, viral antigens, and the like.

The use of parvoviruses as vaccines is known in the art (see, e.g., Miyamura et al., (1994) *Proc. Nat. Acad. Sci USA* 91:8507; U.S. Pat. No. 5,916,563 to Young et al., 5,905,040 to Mazzara et al., U.S. Pat. Nos. 5,882,652, 5,863,541 to Samulski et al.; the disclosures of which are incorporated herein in their entirety by reference). The antigen may be presented in the parvovirus capsid. Alternatively, the antigen may be expressed from a heterologous nucleic acid introduced into a recombinant vector genome. Any immunogen of interest may be provided by the parvovirus vector. Immunogens of interest are well-known in the art and include, but are not limited to, immunogens from human immunodeficiency virus, influenza virus, gag proteins, tumor antigens, cancer antigens, bacterial antigens, viral antigens, and the like.

An immunogenic polypeptide, or immunogen, may be any polypeptide suitable for protecting the subject against a disease, including but not limited to microbial, bacterial, protozoal, parasitic, and viral diseases. For example, the immunogen may be an orthomyxovirus immunogen (e.g., an influenza virus immunogen, such as the influenza virus hemagglutinin (HA) surface protein or the influenza virus nucleoprotein gene, or an equine influenza virus immunogen), or a lentivirus immunogen (e.g., an equine infectious anemia virus immunogen, a Simian Immunodeficiency Virus (SIV) immunogen, or a Human Immunodeficiency Virus (HIV) immunogen, such as the HIV or SIV envelope GP160 protein, the HIV or SIV matrix/capsid proteins, and the HIV or SIV gag, pol and env genes products). The immunogen may also be an arenavirus immunogen (e.g., Lassa fever virus immunogen, such as the Lassa fever virus nucleocapsid protein gene and the Lassa fever envelope glycoprotein gene), a poxvirus immunogen (e.g., vaccinia, such as the vaccinia L1 or L8 genes), a flavivirus immunogen (e.g., a yellow fever virus immunogen or a Japanese encephalitis virus immunogen), a filovirus immunogen (e.g., an Ebola virus immunogen, or a Marburg virus immunogen, such as NP and GP genes), a bunyavirus immunogen (e.g., RVFV, CCHF, and SFS viruses), or a coronavirus immunogen (e.g., an infectious human coronavirus immunogen, such as the human coronavirus envelope glycoprotein gene, or a porcine transmissible gastroenteritis virus immunogen, or an avian infectious bronchitis virus immunogen). The immunogen may further be a polio immunogen, herpes antigen (e.g., CMV, EBV, HSV immunogens) mumps immunogen, measles immunogen, rubella immunogen, diptheria toxin or other diptheria immunogen, pertussis antigen, hepatitis (e.g., hepatitis A or hepatitis B) immunogen, or any other vaccine immunogen known in the art.

Alternatively, the immunogen may be any tumor or cancer cell antigen. Preferably, the tumor or cancer antigen is expressed on the surface of the cancer cell. Exemplary cancer and tumor cell antigens are described in S. A. Rosenberg, (1999) *Immunity* 10:281). Other illustrative cancer and tumor antigens include, but are not limited to: BRCA1 gene product, BRCA2 gene product, gp100, tyrosinase, GAGE-1/2, BAGE, RAGE, NY-ESO-1, CDK4, β-catenin, MUM-1, Caspase-8, KIAA0205, HPVE, SART-1, PRAME, p15, melanoma tumor antigens (Kawakami et al., (1994) *Proc. Natl. Acad. Sci. USA* 91:3515); Kawakami et al., (1994) *J. Exp. Med.*, 180:347); Kawakami et al., (1994) *Cancer Res.* 54:3124), including MART-1 (Coulie et al., (1991) *J. Exp. Med.* 180:35), gp100 (Wick et al., (1988) *J. Cutan. Pathol.* 4:201) and MAGE antigen, MAGE-1, MAGE-2 and MAGE-3 (Van der Bruggen et al., (1991) *Science,* 254:1643); CEA, TRP-1, TRP-2, P-15 and tyrosinase (Brichard et al., (1993) *J. Exp. Med.* 178:489); HER-2/neu gene product (U.S. Pat. No. 4,968,603), CA 125, LK26, FB5 (endosialin), TAG 72, AFP, CA19-9, NSE, DU-PAN-2, CA50, SPan-1, CA724, HCG, STN (sialyl Tn antigen), c-erbB-2 proteins, PSA, L-CanAg, estrogen receptor, milk fat globulin, p53 tumor suppressor protein (Levine, (1993) *Ann. Rev. Biochem.* 62:623); mucin antigens (international patent publication WO 90/05142); telomerases; nuclear matrix proteins; prostatic acid phosphatase; papilloma virus antigens; and antigens associated with the following cancers: melanomas, metastases, adenocarcinoma, thymoma, lymphoma, sarcoma, lung cancer, liver cancer, colon cancer, non-Hodgkins lymphoma, Hodgkins lymphoma, leukemias, uterine cancer, breast cancer, prostate cancer, ovarian cancer, cervical cancer, bladder cancer, kidney cancer, pancreatic cancer and others (see, e.g., Rosenberg, (1996) *Ann. Rev. Med.* 47:481-91).

Alternatively, the heterologous nucleotide sequence may encode any polypeptide that is desirably produced in a cell in vitro, ex vivo, or in vivo. For example, the inventive vectors may be introduced into cultured cells and the expressed gene product isolated therefrom.

It will be understood by those skilled in the art that the heterologous nucleotide sequence(s) of interest may be operably associated with appropriate control sequences. For example, the heterologous nucleic acid may be operably associated with expression control elements, such as transcription/translation control signals, origins of replication, polyadenylation signals, and internal ribosome entry sites (IRES), promoters, enhancers, and the like.

Those skilled in the art will appreciate that a variety of promoter/enhancer elements may be used depending on the level and tissue-specific expression desired. The promoter/enhancer may be constitutive or inducible, depending on the pattern of expression desired. The promoter/enhancer may be native or foreign and can be a natural or a synthetic sequence. By foreign, it is intended that the transcriptional initiation region is not found in the wild-type host into which the transcriptional initiation region is introduced.

Promoter/enhancer elements that are native to the target cell or subject to be treated are most preferred. Also preferred are promoters/enhancer elements that are native to the heterologous nucleic acid sequence. The promoter/enhancer element is chosen so that it will function in the target cell(s) of interest. Mammalian promoter/enhancer elements are also preferred. The promoter/enhance element may be constitutive or inducible.

Inducible expression control elements are preferred in those applications in which it is desirable to provide regulation over expression of the heterologous nucleic acid sequence(s). Inducible promoters/enhancer elements for gene delivery are preferably tissue-specific promoter/enhancer elements, and include muscle specific (including cardiac, skeletal and/or smooth muscle), neural tissue specific (including brain-specific), liver specific, bone marrow specific, pancreatic specific, spleen specific, retinal specific, and lung specific promoter/enhancer elements. Other inducible promoter/enhancer elements include hormone-inducible and metal-inducible elements. Exemplary inducible promoters/enhancer elements include, but are not limited to, a Tet on/off element, a RU486-inducible promoter, an ecdysone-inducible promoter, a rapamycin-inducible promoter, and a metallothionein promoter.

In embodiments of the invention in which the heterologous nucleic acid sequence(s) will be transcribed and then translated in the target cells, specific initiation signals are generally required for efficient translation of inserted protein coding sequences. These exogenous translational control sequences, which may include the ATG initiation codon and adjacent sequences, can be of a variety of origins, both natural and synthetic.

As a further advantage, the inventive duplexed parvovirus vectors may be distinguished from rAAV vectors in that the orientation of the coding sequence with respect the resolvable TR is fixed and may be controlled. Thus, for example, the orientation and expression of the transgene may be controlled with respect to the putative transcriptional control elements within the resolvable TR. Moreover, control over the orientation of the transgene with respect to the non-resolvable TR may provide a greater level of control over the recombination products between the genomes of co-infecting vectors. If either the closed end of the genome (i.e., near the non-resolvable TR) or the open end is a preferred substrate for intermolecular recombination, the orientation of the coding sequence within the recombination product can be predicted and controlled.

Finally, unlike rAAV vectors, the duplexed parvovirus vectors of the present invention are uniform in that they co-package both the plus and minus strands in a single molecule. This characteristic is desirable from the standpoint of producing a consistent clinical grade reagent.

Gene Transfer Technology.

The methods of the present invention also provide a means for delivering heterologous nucleotide sequences into a broad range of cells, including dividing and non-dividing cells. The present invention may be employed to deliver a nucleotide sequence of interest to a cell in vitro, e.g., to produce a polypeptide in vitro or for ex vivo gene therapy. The cells, pharmaceutical formulations, and methods of the present invention are additionally useful in a method of delivering a nucleotide sequence to a subject in need thereof, e.g., to express an immunogenic or therapeutic polypeptide. In this manner, the polypeptide may thus be produced in vivo in the subject. The subject may be in need of the polypeptide because the subject has a deficiency of the polypeptide, or because the production of the polypeptide in the subject may impart some therapeutic effect, as a method of treatment or otherwise, and as explained further below.

In general, the present invention may be employed to deliver any foreign nucleic acid with a biological effect to treat or ameliorate the symptoms associated with any disorder related to gene expression. Illustrative disease states include, but are not limited to: cystic fibrosis (and other diseases of the lung), hemophilia A, hemophilia B, thalassemia, anemia and other blood disorders, AIDs, Alzheimer's disease, Parkinson's disease, Huntington's disease, amyotrophic lateral sclerosis, epilepsy, and other neurological disorders, cancer, diabetes mellitus, muscular dystrophies (e.g., Duchenne, Becker), Gaucher's disease, Hurler's disease, adenosine deaminase deficiency, glycogen storage diseases and other metabolic defects, retinal degenerative diseases (and other diseases of the eye), diseases of solid organs (e.g., brain, liver, kidney, heart), and the like.

Gene transfer has substantial potential use in understanding and providing therapy for disease states. There are a number of inherited diseases in which defective genes are known and have been cloned. In general, the above disease states fall into two classes: deficiency states, usually of enzymes, which are generally inherited in a recessive manner, and unbalanced states, which may involve regulatory or structural proteins, and which are typically inherited in a dominant manner. For deficiency state diseases, gene transfer could be used to bring a normal gene into affected tissues for replacement therapy, as well as to create animal models for the disease using antisense mutations. For unbalanced disease states, gene transfer could be used to create a disease state in a model system, which could then be used in efforts to counteract the disease state. Thus the methods of the present invention permit the treatment of genetic diseases. As used herein, a disease state is treated by partially or wholly remedying the deficiency or imbalance that causes the disease or makes it more severe. The use of site-specific recombination of nucleic sequences to cause mutations or to correct defects is also possible.

The instant invention may also be employed to provide an antisense nucleic acid to a cell in vitro or in vivo. Expression of the antisense nucleic acid in the target cell diminishes expression of a particular protein by the cell. Accordingly, antisense nucleic acids may be administered to decrease expression of a particular protein in a subject in need thereof. Antisense nucleic acids may also be administered to cells in vitro to regulate cell physiology, e.g., to optimize cell or tissue culture systems.

Finally, the instant invention finds further use in diagnostic and screening methods, whereby a gene of interest is transiently or stably expressed in a cell culture system, or alternatively, a transgenic animal model.

In general, the present invention can be employed to deliver any heterologous nucleic acid to a cell in vitro, ex vivo, or in vivo.

Subjects, Pharmaceutical Formulations, Vaccines, and Modes of Administration.

The present invention finds use in both veterinary and medical applications. Suitable subjects for ex vivo gene delivery methods as described above include both avians and mammals, with mammals being preferred. The term "avian" as used herein includes, but is not limited to, chickens, ducks, geese, quail, turkeys and pheasants. The term "mammal" as used herein includes, but is not limited to, humans, bovines, ovines, caprines, equines, felines, canines, lagomorphs, etc. Human subjects are most preferred. Human subjects include neonates, infants, juveniles, and adults.

In particular embodiments, the present invention provides a pharmaceutical composition comprising a virus particle of the invention in a pharmaceutically-acceptable carrier and/or other medicinal agents, pharmaceutical agents, carriers, adjuvants, diluents, etc. For injection, the carrier will typically be a liquid. For other methods of administration, the carrier may be either solid or liquid. For inhalation administration, the carrier will be respirable, and will preferably be in solid or liquid particulate form. As an injection medium, it is preferred to use water that contains the additives usual for injection solutions, such as stabilizing agents, salts or saline, and/or buffers.

In general, a "physiologically acceptable carrier" is one that is not toxic or unduly detrimental to cells. Exemplary physiologically acceptable carriers include sterile, pyrogen-free water and sterile, pyrogen-free, phosphate buffered saline. Physiologically-acceptable carriers include pharmaceutically-acceptable carriers.

By "pharmaceutically acceptable" it is meant a material that is not biologically or otherwise undesirable, i.e., the material may be administered to a subject without causing any undesirable biological effects. Thus, such a pharmaceutical composition may be used, for example, in transfection of a cell ex vivo or in administering a viral particle or cell directly to a subject.

The parvovirus vectors of the invention may be administered to elicit an immunogenic response (e.g., as a vaccine). Typically, vaccines of the present invention comprise an immunogenic amount of infectious virus particles as disclosed herein in combination with a pharmaceutically-acceptable carrier. An "immunogenic amount" is an amount of the infectious virus particles that is sufficient to evoke an immune response in the subject to which the pharmaceutical formulation is administered. Typically, an amount of about $10^3$ to about $10^{15}$ virus particles, preferably about $10^4$ to about $10^{10}$, and more preferably about $10^4$ to $10^6$ virus particles per dose is suitable, depending upon the age and species of the subject being treated, and the immunogen against which the immune response is desired. Subjects and immunogens are as described above.

The present invention further provides a method of delivering a nucleic acid to a cell. Typically, for in vitro methods, the virus may be introduced into the cell by standard viral transduction methods, as are known in the art. Preferably, the virus particles are added to the cells at the appropriate multiplicity of infection according to standard transduction methods appropriate for the particular target cells. Titers of virus to administer can vary, depending upon the target cell type and the particular virus vector, and may be determined by those of skill in the art without undue experimentation.

Recombinant virus vectors are preferably administered to the cell in a biologically-effective amount. A "biologically-effective" amount of the virus vector is an amount that is sufficient to result in infection (or transduction) and expression of the heterologous nucleic acid sequence in the cell. If the virus is administered to a cell in vivo (e.g., the virus is administered to a subject as described below), a "biologically-effective" amount of the virus vector is an amount that is sufficient to result in transduction and expression of the heterologous nucleic acid sequence in a target cell.

The cell to be administered the inventive virus vector may be of any type, including but not limited to neural cells (including cells of the peripheral and central nervous systems, in particular, brain cells), lung cells, retinal cells, epithelial cells (e.g., gut and respiratory epithelial cells), muscle cells, dendritic cells, pancreatic cells (including islet cells), hepatic cells, myocardial cells, bone cells (e.g., bone marrow stem cells), hematopoietic stem cells, spleen cells, keratinocytes, fibroblasts, endothelial cells, prostate cells, germ cells, and the like. Alternatively, the cell may be any progenitor cell. As a further alternative, the cell can be a stem cell (e.g., neural stem cell, liver stem cell). As still a further alternative, the cell may be a cancer or tumor cell. Moreover, the cells can be from any species of origin, as indicated above.

In particular embodiments of the invention, cells are removed from a subject, the parvovirus vector is introduced therein, and the cells are then replaced back into the subject. Methods of removing cells from subject for treatment ex vivo, followed by introduction back into the subject are known in the art (see, e.g., U.S. Pat. No. 5,399,346; the disclosure of which is incorporated herein in its entirety). Alternatively, the rAAV vector is introduced into cells from another subject, into cultured cells, or into cells from any other suitable source, and the cells are administered to a subject in need thereof.

Suitable cells for ex vivo gene therapy are as described above.

The cells transduced with the inventive vector are preferably administered to the subject in a "therapeutically-effective amount" in combination with a pharmaceutical carrier. A "therapeutically-effective" amount as used herein is an amount that provides sufficient expression of the heterologous nucleotide sequence delivered by the vector to provide some improvement or benefit to the subject. Alternatively stated, a "therapeutically-effective" amount is an amount that will provide some alleviation, mitigation, or decrease in at least one clinical symptom in the subject. Those skilled in the art will appreciate that the therapeutic effects need not be complete or curative, as long as some benefit is provided to the subject.

In alternate embodiments, cells that have been transduced with a vector according to the invention may be administered to elicit an immunogenic response against the delivered polypeptide. Typically, a quantity of cells expressing an immunogenic amount of the polypeptide in combination with a pharmaceutically-acceptable carrier is administered. An "immunogenic amount" is an amount of the expressed polypeptide that is sufficient to evoke an active immune response in the subject to which the pharmaceutical formulation is administered. The degree of protection conferred by the active immune response need not be complete or permanent, as long as the benefits of administering the immunogenic polypeptide outweigh any disadvantages thereof.

Dosages of the cells to administer to a subject will vary upon the age, condition and species of the subject, the type of cell, the nucleic acid being expressed by the cell, the mode of administration, and the like. Typically, at least about $10^2$ to about $10^8$, preferably about $10^3$ to about $10^6$ cells, will be administered per dose. Preferably, the cells will be administered in a "therapeutically-effective amount".

A further aspect of the invention is a method of treating subjects in vivo with the inventive virus particles. Administration of the parvovirus particles of the present invention to a human subject or an animal in need thereof can be by any means known in the art for administering virus vectors.

Exemplary modes of administration include oral, rectal, transmucosal, topical, transdermal, inhalation, parenteral (e.g., intravenous, subcutaneous, intradermal, intramuscular, and intraarticular) administration, and the like, as well as direct tissue or organ injection, alternatively, intrathecal, direct intramuscular, intraventricular, intravenous, intraperitoneal, intranasal, or intraocular injections. Injectables can be prepared in conventional forms, either as liquid solutions or suspensions, solid forms suitable for solution or suspension in liquid prior to injection, or as emulsions. Alternatively, one may administer the virus in a local rather than systemic manner, for example, in a depot or sustained-release formulation.

The parvovirus vector administered to the subject may transduce any permissive cell or tissue. Suitable cells for transduction by the inventive parvovirus vectors are as described above.

In particularly preferred embodiments of the invention, the nucleotide sequence of interest is delivered to the liver of the subject. Administration to the liver may be achieved by any method known in the art, including, but not limited to intravenous administration, intraportal administration, intrabiliary administration, intra-arterial administration, and direct injection into the liver parenchyma.

In other preferred embodiments, the inventive parvovirus particles are administered intramuscularly, more preferably by intramuscular injection or by local administration (as defined above). Delivery to the brain is also preferred. In other preferred embodiments, the parvovirus particles of the present invention are administered to the lungs.

The parvovirus vectors disclosed herein may be administered to the lungs of a subject by any suitable means, but are preferably administered by administering an aerosol suspension of respirable particles comprised of the inventive parvovirus vectors, which the subject inhales. The respirable particles may be liquid or solid. Aerosols of liquid particles comprising the inventive parvovirus vectors may be produced by any suitable means, such as with a pressure-driven aerosol nebulizer or an ultrasonic nebulizer, as is known to those of skill in the art. See, e.g., U.S. Pat. No. 4,501,729. Aerosols of solid particles comprising the inventive virus vectors may likewise be produced with any solid particulate medicament aerosol generator, by techniques known in the pharmaceutical art.

Dosages of the inventive parvovirus particles will depend upon the mode of administration, the disease or condition to be treated, the individual subject's condition, the particular virus vector, and the gene to be delivered, and can be determined in a routine manner. Exemplary doses for achieving therapeutic effects are virus titers of at least about $10^5$, $10^6$, $10^7$, $10^8$, $10^9$, $10^{10}$, $10^{11}$, $10^{12}$, $10^3$, $10^{14}$, $10^{15}$ transducing units or more, preferably about $10^8$-$10^{13}$ transducing units, yet more preferably $10^{12}$ transducing units.

In particular embodiments, the inventive parvovirus particles are administered as part of a method of treating cancer or tumors by administering anti-cancer agents (e.g., cytokines) or a cancer or tumor antigen. The parvovirus particle may be administered to a cell in vitro or to a subject in vivo by using ex vivo methods, as described herein and known in the art.

The term "cancer" has its understood meaning in the art, for example, an uncontrolled growth of tissue that has the potential to spread to distant sites of the body (i.e., metastasize). Exemplary cancers include, but are not limited to, leukemias, lymphomas, colon cancer, renal cancer, liver cancer, breast cancer, lung cancer, prostate cancer, ovarian cancer, melanoma, and the like. Preferred are methods of treating and preventing tumor-forming cancers. The term "tumor" is also understood in the art, for example, as an abnormal mass of undifferentiated cells within a multicellular organism. Tumors can be malignant or benign. Preferably, the inventive methods disclosed herein are used to prevent and treat malignant tumors.

Cancer and tumor antigens according to the present invention have been described hereinabove. By the terms "treating cancer" or "treatment of cancer", it is intended that the severity of the cancer is reduced or the cancer is at least partially eliminated. Preferably, these terms indicate that metastasis of the cancer is reduced or at least partially eliminated. It is further preferred that these terms indicate that growth of metastatic nodules (e.g., after surgical removal of a primary tumor) is reduced or at least partially eliminated. By the terms "prevention of cancer" or "preventing cancer" it is intended that the inventive methods at least partially eliminate or reduce the incidence or onset of cancer. Alternatively stated, the present methods slow, control, decrease the likelihood or probability, or delay the onset of cancer in the subject.

Likewise, by the terms "treating tumors" or "treatment of tumors", it is intended that the severity of the tumor is reduced or the tumor is at least partially eliminated. Preferably, these terms are intended to mean that metastasis of the tumor is reduced or at least partially eliminated. It is also preferred that these terms indicate that growth of metastatic nodules (e.g., after surgical removal of a primary tumor) is reduced or at least partially eliminated. By the terms "prevention of tumors" or "preventing tumors" it is intended that the inventive methods at least partially eliminate or reduce the incidence or onset of tumors. Alternatively stated, the present methods slow, control, decrease the likelihood or probability, or delay the onset of tumors in the subject.

In other embodiments, cells may be removed from a subject with cancer or a tumor and contacted with the parvovirus particles of the invention. The modified cell is then administered to the subject, whereby an immune response against the cancer or tumor antigen is elicited. This method is particularly advantageously employed with immunocompromised subjects that cannot mount a sufficient immune response in vivo (i.e., cannot produce enhancing antibodies in sufficient quantities).

It is known in the art that immune responses may be enhanced by immunomodulatory cytokines (e.g., $\alpha$-interferon, $\beta$-interferon, $\gamma$-interferon, $\omega$-interferon, $\tau$-interferon, interleukin-1$\alpha$, interleukin-1$\beta$, interleukin-2, interleukin-3, interleukin-4, interleukin 5, interleukin-6, interleukin-7, interleukin-8, interleukin-9, interleukin-10, interleukin-11, interleukin 12, interleukin-13, interleukin-14, interleukin-18, B cell Growth factor, CD40 Ligand, tumor necrosis factor-$\alpha$, tumor necrosis factor-$\beta$, monocyte chemoattractant protein-1, granulocyte-macrophage colony stimulating factor, and lymphotoxin). Accordingly, in particular embodiments of the invention, immunomodulatory cytokines (preferably, CTL inductive cytokines) are administered to a subject in conjunction with the methods described herein for producing an immune response or providing immunotherapy.

Cytokines may be administered by any method known in the art. Exogenous cytokines may be administered to the subject, or alternatively, a nucleotide sequence encoding a cytokine may be delivered to the subject using a suitable vector, and the cytokine produced in vivo.

Having now described the invention, the same will be illustrated with reference to certain examples, which are included herein for illustration purposes only, and which are not intended to be limiting of the invention.

EXAMPLE 1

Materials and Methods

Plasmids. The rAAV plasmids expressing green fluorescent protein (GFP) were constructed from the previously described pTR$_{BS}$UF-2 (a gift from Nick Muzyczka). First, the humanized GFP coding sequence was replaced with the enhanced GFP (eGFP) (Clonetech) to create the plasmid, pTR-CMV-GFPneo. This plasmid generated the rAAV-GFPneo vector. Second, the Sal I fragment containing the neo coding region and SV40 promoter was deleted to create pTR-CMV-GFP. The vector from this plasmid was referred to as rAAV-GFP in this report.

The plasmid, p43mEpo, a gift from Barry Byrne, contained the mouse erythropoietin gene under the control of the CMV promoter and generated a rAAV replicon (rAAVmEpo) of less than half the wtAAV length. A longer version of this construct (pmEpo-λ) was made by inserting the 2.3 kb Hind III fragment from λ phage into a Cla I site between the polyadenylation signal and the downstream AAV terminal repeat. The rAAV-LacZ vector was generated from pDX 11-LacZ, which has been described elsewhere (McCown et al., (1996) *Brain Research* 713:99).

Viral vectors. Viral Vectors were generated in 293 cells ($10^8$-$10^9$ cells per prep) by co-transfecting 3 plasmids containing: 1) the specific rAAV construct, 2) the AAV rep and cap genes (pACG), or 3) the essential adenovirus helper genes (pXX-6; Xiao et al., (1998) *J. Virology* 72:2224). At 40 hr post-transfection, the cells were scraped into the media and lysed by three freeze-thaw cycles. The lysates were incubated at 37° C. with 2 ug/ml DNase I until flocculent debris was dispersed. The lysates were cleared by centrifugation and rAAV was precipitated using ammonium sulfate (Snyder et al., Production of recombinant adeno-associated virus vectors. In: Dracopoli et al., editors. Current Protocols in Human Genetics. New York: John Wiley & Sons Ltd.: 1996. p. 12.1.1-12.2.23). The virus ppt. was resuspended with 8 ml 10 mM Tris pH 8.0, 1 mM MgCl$_2$ and cesium chloride was added to reach a final density of 1.4 g/cm$^3$ and a final volume 12.5 ml. The solution was centrifuged for 36 hrs at 38 krpm in an SW41 rotor. Fractions (0.75 ml) were collected by puncturing with a hypodermic needle at the bottom of each tube and pumping the liquid to a fraction collector. The vectors were stored at 4° C. in cesium chloride.

Virion DNA (vDNA) was extracted from 10 µl of each fraction by digestion in 50 µl reactions containing 0.4 mg/ml protease K, 1% sarkosyl, and 10 mM EDTA at 50° C. for 1 hour, followed by phenol/chloroform extraction. The samples were diluted 3-fold with water and precipitated with ethanol for analysis by alkaline agarose gel electrophoresis and Southern blot hybridization.

Cells and infections. HeLa and HEK 293 cells were grown in DMEM media containing 10% FBS and Pen/Strep. Viral vector stocks were diluted in media before adding to subconfluent cultures and left on the cells until GFP transduction was observed by fluorescence microscopy at 24 hours post-infection.

For expression of erythropoietin in mouse livers, 200 µl normal saline, containing 2×10$^{10}$ physical particles of either conventional rAAV or duplexed virus (scAAV), was injected directly into the portal veins of 10 week old Balb-c ByJ mice (Jackson Laboratory). Blood samples were collected by retro-orbital phlebotomy at the time of infection and at 7-day intervals for determination of hematocrit.

EXAMPLE 2

Generation of Duplexed Vectors

Figure 2:
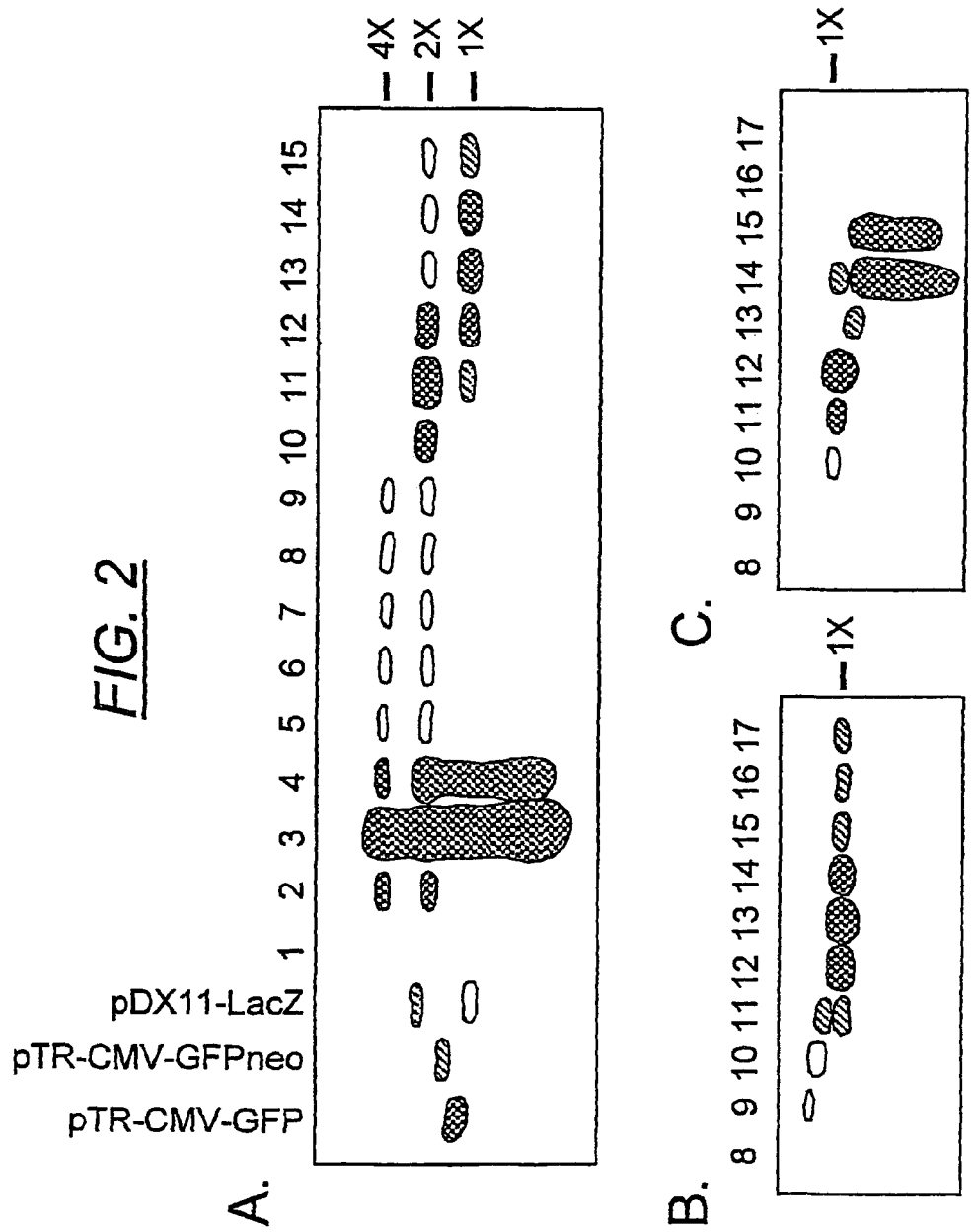
FIG. 2. Vector fractionation on CsCl gradients. Virion DNA (vDNA) was extracted from CsCl gradient fractionated CMV-GFP (Panel a), GFPneo (Panel b), and LacZ (Panel c) rAAV vectors. Alkaline agarose gels of the vDNA were Southern blotted and hybridized with a CMV-GFP DNA fragment. Markers at the left end of panel a were the excised vector sequences from the plasmids used to generate the viral vectors (see results). The number of unit length, ssDNA, vector copies per molecule are indicated by 1×, 2×, and 4×. The viral vectors used in the experiments depicted in FIGS. 3 and 4 were from fractions a-11 or a-10 for CMV-GFP (as indicated in the figure legends), fraction b-13 for GFPneo, and fraction c-12 for LacZ.

A rAAV plasmid construct (pTR-CMV-GFP), with a replicon size of 2299 nucleotides, was used to generate a viral vector stock (rAAV-GFP) by conventional methods. The predicted size of the dimeric replicative form of this vector was 4474 nucleotides (FIG. 1), which was 95.6% of the wt AAV genome length. The viral vectors were fractionated by isopycnic gradient centrifugation in CsCl and the vDNA content of each fraction was analyzed on alkaline agarose gels (FIG. 2). PhosphoImager scans were used to quantify the vDNA specific bands from each fraction. Under denaturing conditions, the self-complementary dimer DNA (FIG. 2, panel a, fractions 10-13) ran at approximately twice the length of the monomeric genome. The hybridizing material in fractions 24 is unpackaged replicative form DNA that sediments at the bottom of the gradient. Although a DNase step was included in the vector purification (see methods), the treatment was not intended to be exhaustive and this material proved to be DNase sensitive in subsequent experiments while the material in fractions 10-14 was DNase resistant (data not shown). Vectors containing mostly dimeric DNA genomes (fractions 10 and 11) were designated as duplexed or "self-complementary" virus (scAAV). The inverted repeat structure of these molecules was confirmed by restriction enzyme digestion (data not shown).

Two additional rAAV vectors (FIG. 1) were generated and purified in parallel, and analyzed in the same manner (FIG. 2, panels b and c). The first, rAAV-GFPneo, contained a neo gene in addition to the GFP and had a replicating genome length of 3398 nucleotides. This was 72.6% of the wtAAV genome size, and was too large to be packaged as a dimer. The second was a 4898 nucleotide rAAV-CMV-LacZ construct, which was slightly larger (104.7%) than wtAAV genome size, but within the limit for efficient packaging (Dong et al., (1996) *Human Gene Therapy* 7:2101). The lower density, higher mobility hybridizing material in fractions 14 and 15 (FIG. 2, panel c) comprised genomes which had undergone deletions and these fractions were not used in subsequent experiments.

EXAMPLE 3

Figure 3:
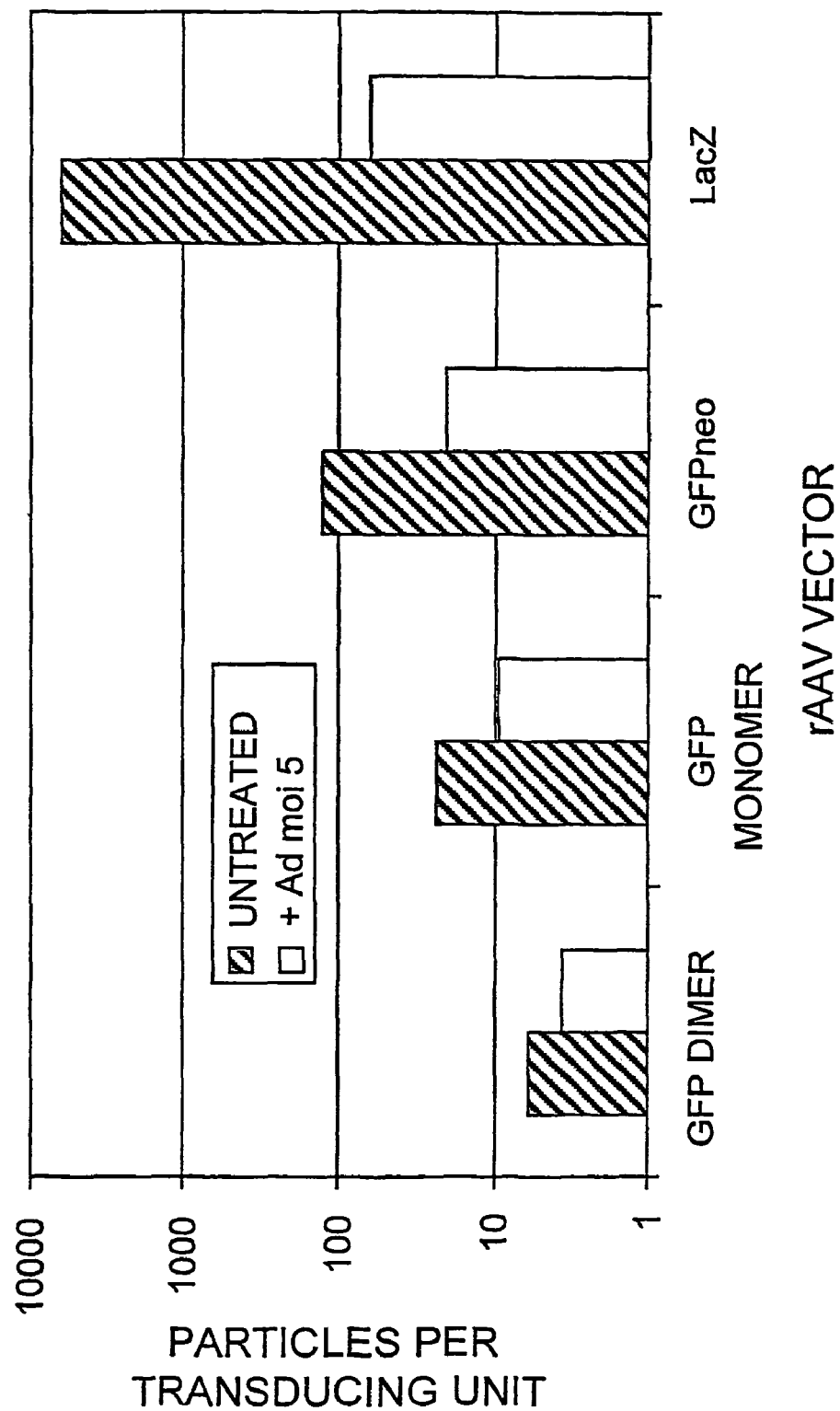
FIG. 3. Transduction efficiency of duplexed versus conventional rAAV vectors in the absence and presence of co-infecting adenovirus. The efficiencies of the three CsCl fractionated vectors (FIG. 1) were compared in rapidly dividing HeLa cells infected with scAAV-GFP fraction 11 (0.5 particles per cell), rAAV-GFPneo fraction 13 (2 particles per cell), or rAAV-LacZ fraction 12 (0.5 particles per cell). Transduction was quantified at 24 hours post-infection by counting GFP positive cells using fluorescence microscopy, or by fixing the cells and X-Gal. staining. The transducing efficiency was graphed as the number of physical particles per transducing unit, as determined by the number of cells scoring positive for GFP or LacZ expression. Dark grey bars indicate transducing efficiency in the presence of Ad co-infection at 5 pfu per cell.

Transduction with Duplexed Versus Monomeric Vectors and Effects of Ad co-Infection The transducing efficiency of the scAAV-GFP (FIG. 2, panel a, fraction 11) was compared with the homologous monomer (fraction 13), as well as the GFPneo and LacZ vectors (FIG. 2, panels b and c, fractions 13 and 12, respectively) in HeLa cells infected at low multiplicity (FIG. 3). The particle numbers were calculated from the specific, full-length vDNA Phospholmager signals in each fraction on the Southern blot, after correction for monomeric versus dimeric DNA copy number. Thus, each duplexed virus contains two copies of the transgene as a single molecule, in the inverted repeat orientation, while each monomeric particle contains one single-stranded copy.

The scAAV-GFP vector (fraction 11), containing approximately 90% dimer virus, yielded a 5.9:1 ratio of physical particles to transducing units, thus bearing out the prediction of high transducing efficiency. Fraction 13 from the same gradient, conversely containing approximately 80-90% monomer virus, had a 24.6:1 particle to transducing unit ratio. This 4-fold difference in efficiency represented a minimum difference when it was considered that the dimer contamination in the monomer fraction would have a greater impact on its transducing potential than the monomer component would contribute to the dimer fraction. In contrast, the monomeric ssDNA GFPneo and LacZ vectors had particle to transducing unit ratios of 125:1 and 828:1, respectively, comparable to previously reported efficiencies for these vectors (Fisher et al., (1996) *J. Virology* 70:520; Zolotukhin et al., (1999) *Gene Therapy* 6:973).

The transducing efficiency of conventional rAAV vectors can be greatly enhanced (up to 100-fold) by co-infection with Ad, or by treatment with DNA damaging agents or other types of cell stress. This enhancement had been associated with the cell-mediated transformation of the ssDNA genome into active ds-DNA transcription templates. Because the duplexed vector contains the two complementary strands packaged as a single molecule, it was predicted that transduction would be independent of enhancement by adenovirus. This was largely the case when HeLa cells were co-infected with the duplexed vectors and 5 infectious units per cell of adenovirus (FIG. 3). The number of GFP positive cells in the duplexed virus infected cultures was increased by only 1.6-fold, an effect which could be attributed to the transcriptional effects of adenovirus infection on the activity of the CMV promoter as previously reported (Clesham et al., (1998) *Gene Therapy* 5:174; Loser et al., (1998) *J. Virology* 72:180). The monomer vector transduction rate was increased 2.4-fold by Ad co-infection, while the GFPneo and LacZ vectors were induced 6.0-fold and 12.8-fold, respectively.

In sum, in cultured HeLa cells, the duplexed vector was greater than four-fold more efficient than the homologous vector containing only a monomeric ss-DNA genome. This difference would likely be greater if not for the approximately 10-20% contamination of monomer fractions with dimer vectors. Consistent with this interpretation, the duplexed vector was 20-fold more efficient than a conventional rAAV-GFPneo vector and 140-fold more efficient than a rAAV-LacZ vector.

EXAMPLE 4

Transduction with Duplexed Vectors in the Absence of Host Cell DNA Synthesis

Because the vDNA of the duplexed vectors contained both DNA strands on a single molecule, allowing efficient reannealing upon uncoating, it was predicted that these vectors would obviate the role of host-cell DNA synthesis in transduction. The scAAV-GFP vector was compared with the homologous monomer, and the GFPneo vector, in HeLa cells pretreated with hydroxyurea (HU) 24 hours before infection to inhibit host cell DNA synthesis. Hydroxyurea treatment was continued, uninterrupted, at the same concentrations following infection and maintained on the cells for the following 24 hours, until GFP transduction was scored.

Figure 4:
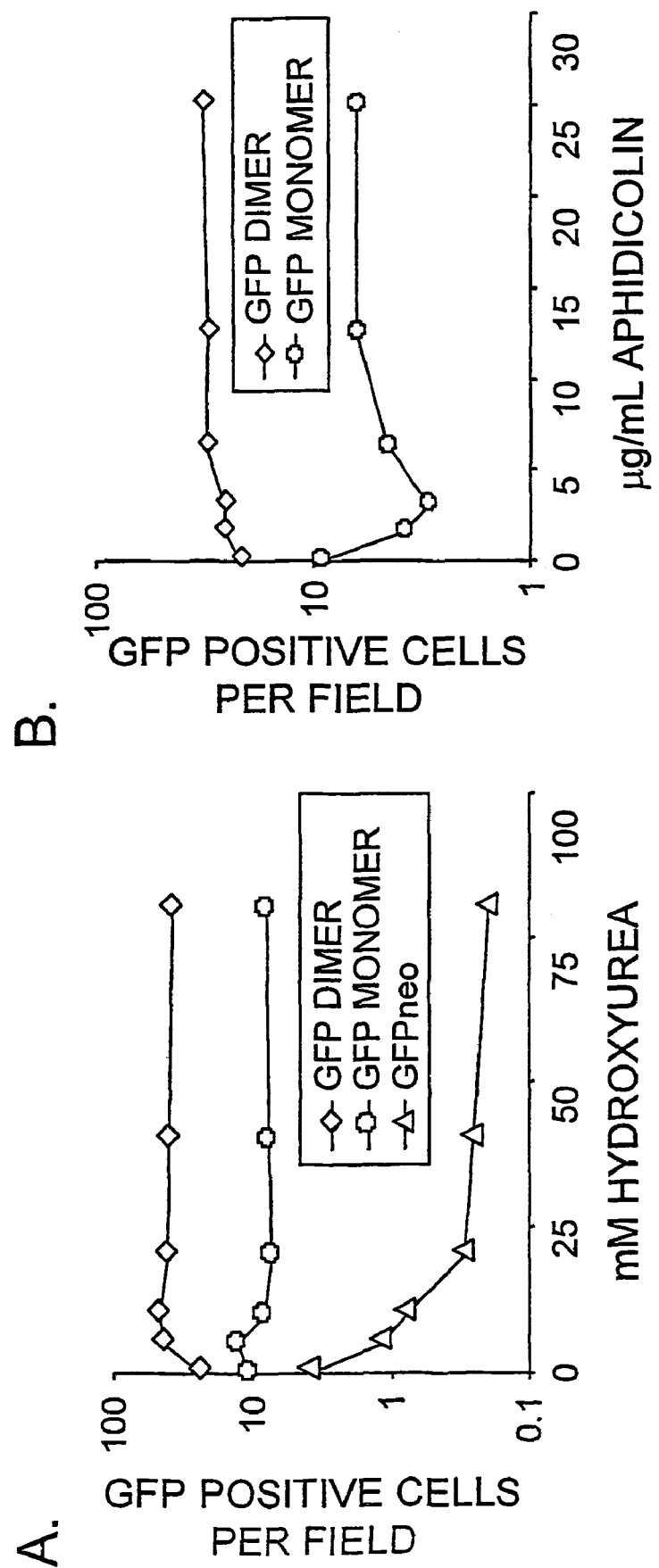
FIG. 4. Transduction with duplexed and conventional rAAV vectors in the presence of DNA synthesis inhibitor. (Panel a). HeLa cell cultures at 30% confluence were treated with the indicated concentrations of hydroxyurea 24 hr before infecting with 3.8×10$^6$ particles of the scAAV-GFP, ♦, (FIG. 2a, fraction 10), the homologous monomer, ● (FIG. 2, panel a, fraction 14), or rAAV-GFPneo, ▲, (FIG. 2, panel b, fraction 13). The HU treatment was maintained until transduction was assayed at 24 hr post-infection. Each data point was calculated from the mean of the number of GFP positive cells in 10 random fields independently of the total cell number, which was variable due to the effect of hydroxyurea on cell division. (Panel b). The same procedure was used to evaluate transduction in the presence of the indicated concentrations of aphidicolin. Only the duplexed and homologous monomer (fractions 10 and 14) were compared.

Transduction from the scAAV-GFP was stimulated by up to 1.9 fold in response to increasing concentrations of HU (FIG. 4). This stimulation, similar in magnitude to that observed with Ad co-infection, was probably affected through a combination of transcriptional transactivation of the CMV promoter brought about by cell stress, and the accumulation of GFP in the non-dividing cells. In contrast, transduction from the homologous monomer vector fraction was stimulated at the lowest HU concentration and inhibited at higher concentrations. The residual transducing activity from the monomer vector at higher HU concentrations, at a level approximately 5-fold lower than that of the duplexed virus fraction, is consistent with the 10-20% contamination of the monomer fractions with dimer containing particles (FIG. 2, panel a). The rAAV-GFPneo vector transduction was inhibited greater than 10-fold under the same conditions. Identical results were obtained by treatment with aphidicolin, a polymerase $\alpha/\delta$ specific inhibitor (FIG. 4, panel b). This confirmed the hypothesis that duplexed vector transduction was independent of host-cell DNA synthesis.

EXAMPLE 5

Transduction by Duplexed Vectors in vivo

A different reporter was used for the comparison of duplexed and conventional single-stranded rAAV efficiency in vivo. The dimer-producing construct contained only the mouse erythropoietin gene (mEpo) transcribed from the CMV promoter. The size of the replicating element of this minimal vector was 2248 nucleotides. The dimeric form of this molecule, 4372 nucleotides in length (FIG. 1), was 93% of the wtAAV genome size, and was readily packaged. A second construct contained the identical transgene, with the addition of a downstream heterologous sequence ($\lambda$ phage) to bring the size of the recombinant vector to 4570 nucleotides, or 98% of the wtAAV genome size. Previous studies have used lambda phage DNA as a stuffer without deleterious effects on the vector (Muzyczka et al., (1992) *Curr. Top. Microbiol. Immunol.* 158:97). Both vectors were purified by heparin-agarose chromatography. The smaller vector was additionally purified on a CsCl gradient to isolate dimeric DNA-containing virions (not shown). The two vector stocks were quantified using Southern blots from alkaline agarose gels to determine the number of DNA-containing particles. In this case, approximately 25% of the particles in the dimer fraction contained two separate monomer genomes. Because they could not be separated from true dimer by density, and because their behavior has not been characterized, these were counted as dimer particles, for the purpose of comparison to the full-length vector, such that the dimer effect might only be underestimated rather than overestimated.

Equal numbers of physical rAAV particles ($2 \times 10^{10}$ per animal in 200 µl normal saline) were administered to mice by portal vein injection. The expression of the mEpo gene was evaluated by observing changes in hematocrit at 7-day intervals. Control mice received either intraportal saline injections or were not operated, but phlebotomized at 7-day intervals. Mice receiving the duplexed vector responded with a rapid increase in hematocrit (FIG. 5), and with continuing increases over the following two weeks. Considering the lag time between expression of erythropoietin and the production of red blood cells, this suggested that the duplexed vector was expressed at high levels within the first week. Mice which received the full-length, ssDNA vector did not show a significant increase in hematocrit until 21 days post-injection, and did not reach levels comparable to the animals treated with duplexed vector over the course of the experiment.

Infecting mice with scAAVmEpo leads to a faster response, and a greater rise in hematocrit, than the full-length ssDNA vector carrying the same gene. These results support our observations in cultured cells and is consistent with the view that the dimeric vectors are ready to express the transgene immediately upon uncoating and entry into the nucleus. The higher levels of expression ultimately achieved may reflect the inability of many infects cells to form dsDNA from conventional rAAV and/or the loss/degradation of ssvDNA prior to the formation of duplex (Miao et al., (1998) *Nature Genetics* 19:13).

As we have demonstrated by pre-treatment of cells with HU, transduction with the scAAV vector is independent of host cell DNA synthesis. The ability to transduce cells in the absence of DNA synthesis represents a fundamental departure in the biology of scAAV vectors from the parent virus, allowing them to function under circumstances where conventional rAAV vectors would fail. Certain cell types are extremely inefficient for rAAV transduction ostensibly due to the inability to synthesize or recruit a complementary strand (Fisher et al., (1996) *J. Virology* 70:520; Alexander et al., (1996) *Human Gene Therapy* 7:841; Miao et al., (1998) *Nature Genetics* 19:13). The scAAV suffers no such limitation and can be used with marker genes to directly determine whether a cell is permissive for rAAV transduction in all other steps irrespective of DNA synthesis.

Regardless of the ability of the target cell to make the rAAV complementary strand, it is clear that these reagents provide an alternative AAV delivery system for genes that may require rapid onset. More importantly, our data suggest that scAAV vectors achieve overall higher levels of therapeutic product when an identical number of particles is administered. Thus, scAAV vectors will prove useful where a more timely, robust, or quantitative response to vector dose is required. The potential for attaining critical levels of transgene expression at minimal dose is also important with respect to vector production requirements for clinical trials and for minimizing patient exposure to virus.

EXAMPLE 6

Improved Substrates for Producing Duplexed Parvovirus Vectors

Figure 6:
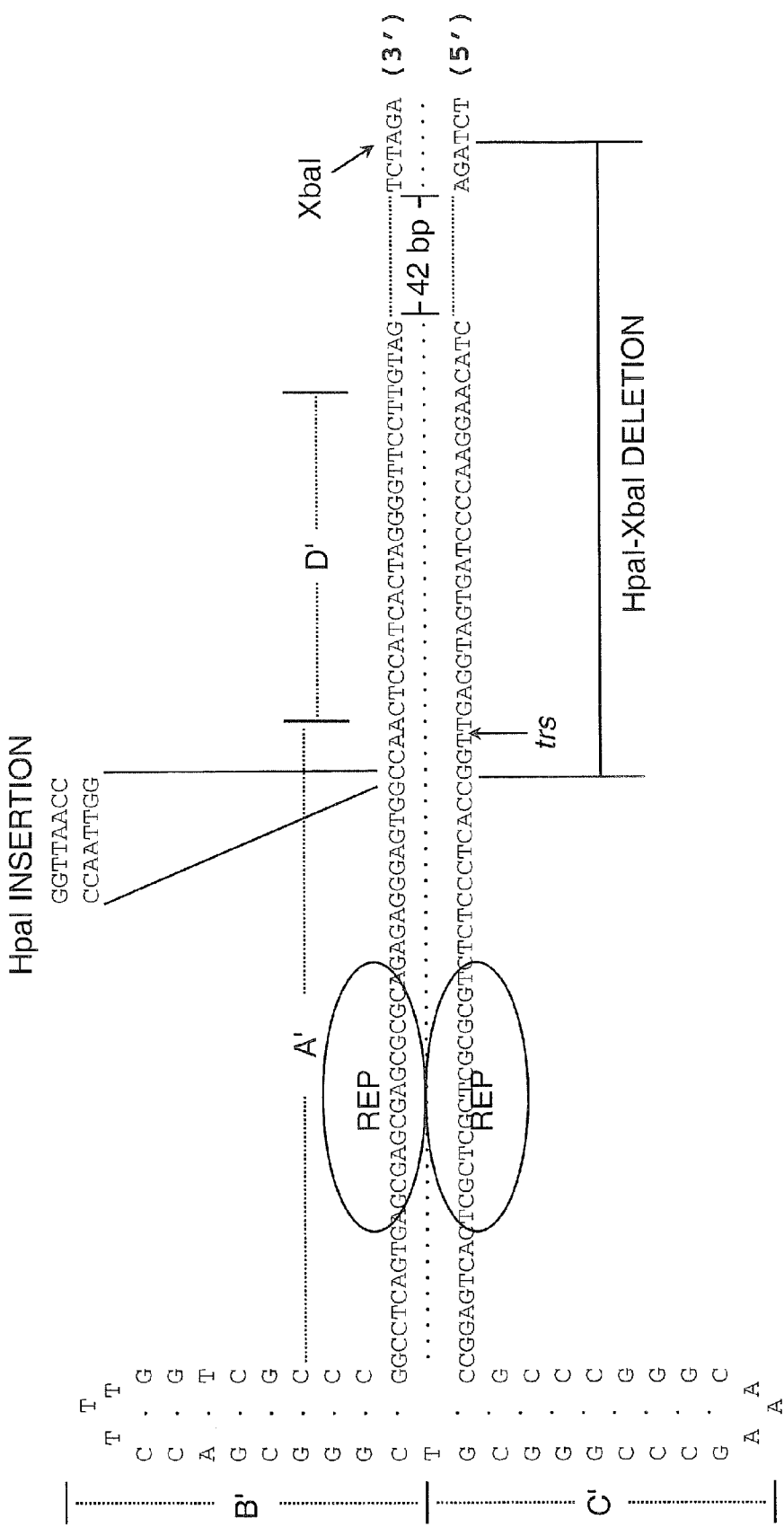
FIG. 6 is a representation of a preferred template for producing the duplexed parvovirus vectors of the invention. The nucleotide sequence of the AAV2 terminal repeat is shown (SEQ ID NO:1) Also shown is an XbaI site and an insertion of a HpaI site, which can be used to delete the indicated fragment and create a modified terminal repeat with reduced resolution by Rep.

To streamline the production of duplexed vector stocks, and to eliminate the complications of mixed populations of duplex and monomer genomes, a mutant vector was created which generates only the dimer genomes (FIG. 6). This construct has a mutation in one TR, such that the Rep nicking site (trs) is deleted, while the other TR is wild type. The effect is that rolling hairpin replication initiates from the wt end of the genome, proceeds through the mutant end without terminal resolution, and then continues back across the genome again to create the dimer. The end product is a self-complementary genome with the mutant TR in the middle and wt TRs now at each end. Replication and packaging of this molecule then proceeds as normal from the wt TRs, except that the dimeric structure is maintained in each round.

Figure 7:
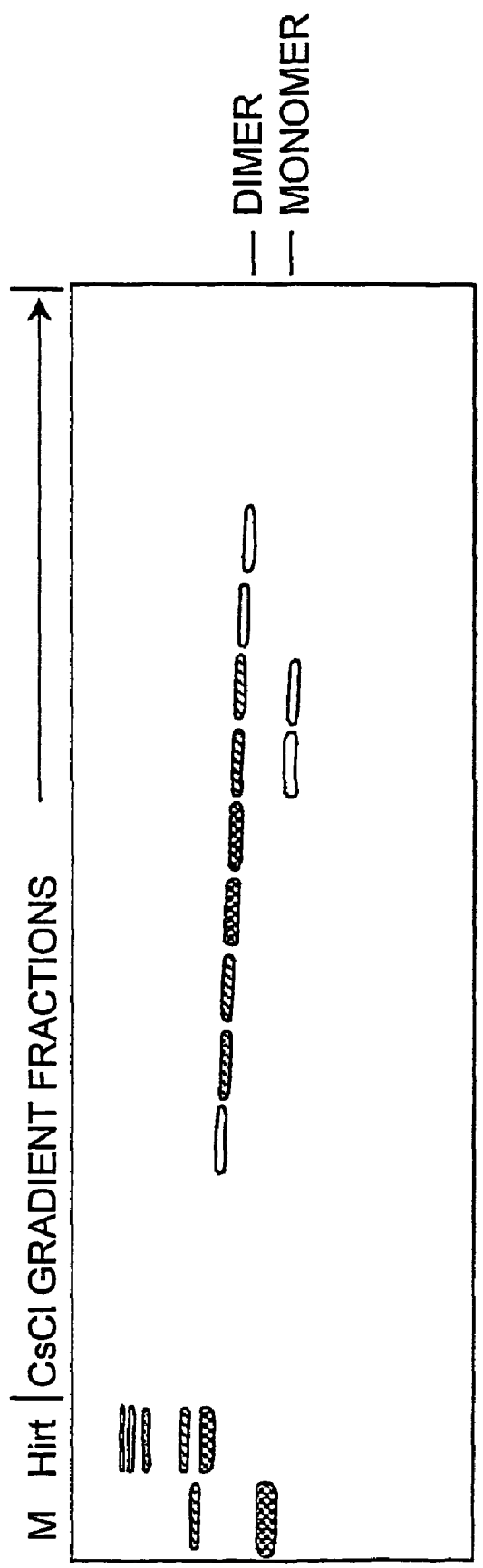
FIG. 7 shows a CsCl density gradient of the rAAV-CMV-GFP Hpa-trs mutant vector.

Vector stocks of both rAAV-CMV-GFP-Hpa-trs and rAAV-CMV-mEpo-Hpa-trs have been generated using this mutant background and analyzed the products on CsCl gradients as above (FIG. 7). These constructs produce approximately 90% duplexed vectors. This will allow greater yields of the duplexed parvovirus vector and the use of iodixanol/heparin purification for these vectors without the additional step of CsCl density gradient purification.

The plasmid construct used to generate these vectors contained a deletion in the 5' TR, relative to the coding strand of the expressed transgene. This deletion includes all the D element and 3 bp of the A element, thus spanning the nicking site (FIG. 6). All AAV sequences between the remainder of the A element and the transgene are deleted. This precludes homologous recombination between sequences flanking the mutated TR and the wt TR, thus reducing the possibility of gene conversion as described by Samulski et al., (1983) *Cell* 33:135. This deletion was constructed by cutting at unique restriction sites immediately 5' to the transgene (KpnI) and within the Amp gene of the bacterial plasmid sequences (XmnI). The fragment removed, containing one TR, was replaced with a fragment from a second rAAV plasmid, which had been cut at the same site within the Amp gene, and at a synthetic HpaI site previously inserted into the BalI site to the left of the A/D junction.

In an alternative embodiment, a template for preferentially producing duplexed vector is generated with a resolvable AAV TR at one end and a modified AAV TR is produced by inserting a sequence into the TR. In one particular embodiment, the wt AAV plasmid psub201, is used to produce this template (Samulski et al., (1987) *J. Virology* 61:3096). This construct contains a unique pair of Xba I sites as well as PvuII sites flanking the viral TRs. Two AAV plasmid intermediates derived from psub201, Hpa7 and Hpa9, have a unique HpaI linker (CCAATTGG) inserted at the BalI site between nucleotide 121 and 122 (Hpa9) and between 4554 and 4555 (Hpa7) in the TR sequence of the AAV genome, respectively (Xiao, X., (1996), "Characterization of Adeno-associated virus (AAV) DNA replication and integration", Ph.D. Dissertation, University of Pittsburgh, Pittsburgh, Pa.). Insertion of these linkers displaces the wt AAV nicking site inward away from the native position, resulting in an inability to be resolved by the AAV Rep protein after replication.

These substrates accumulate a dimeric intermediate until gene conversion takes place. Digestion of Hpa7 or Hpa9 with HpaI restriction enzyme plus partial digestion with Xba I, results in novel TRs lacking the wt AAV nicking site as well as the D element (from the left for Hpa9 and from the right for Hpa7). This substrate is not suitable for gene conversion as described by Samulski et al., (1983) *Cell* 33:135, due to the absence of the D element, and continues to accumulate a dimeric replication intermediate after viral infection. When starting with a molecule that is half-size or less of the wtAAV genome, this intermediate is preferentially packaged by AAV capsids. These molecules are dimeric in form (covalently linked through the modified TR), more specifically, because they are self-complementary they provide a unique source of parvovirus vectors carrying double-stranded substrates. These vector particles bypass the rate-limiting step required for all currently utilized AAV vectors, namely, second-strand synthesis (see Ferrari et al., (1996) *J. Virology* 70:3227-34).

EXAMPLE 7

Transduction of Dendritic Cells

Dendritic cells (DC) are postulated to play important roles in antigen presentation and initiation of several T cell dependent immune responses. DC have been demonstrated to be more potent antigen-presenting cells (APC) than are macrophages or monocytes. Moreover, it has been reported that DC stimulate T cell proliferation up to ten-fold more efficiently than do monocytes (Guyre et al., (1997) *Cancer*

Immunol. Immunother. 45:146, 147 col. 2). Accordingly, there are numerous efforts to target vectors to dendritic cells so as to produce a more effective immune response. It has previously been reported that DC are refractory to AAV vectors (Jooss et al., (1998) *J. Virology* 72:4212).

DC from two human patients were obtained and cultured in vitro. Cells from each patient were transduced with wtAAV-GFP vector or pHpa7GFP (duplexed vector, described in Example 1) at a MOI of 10. No GFP expression was detected in cells transduced with wtAAV-GFP after 7 days. In contrast, GFP expression was observed in 5-15% DC transduced with dimeric pHpa7GFP vector.

These results suggest that the limiting step for wtAAV transduction of DC is at level of host cell ability to mediate second-strand synthesis. The parvovirus vectors of the invention appear to obviate this step by providing the cell with a double-stranded substrate. Accordingly, the inventive dimeric parvovirus vectors have a different (e.g., broader) tropism and target cell range than do wtAAV vectors.

EXAMPLE 8

In vivo Administration of pHpa7GFP

To evaluate the tropism of the duplexed vectors in vivo, mice are administered intramuscularly (im) with approximately $1.5 \times 10^{11}$ of the wtAAV-GFP or pHPA7GFP vectors described in Example 7. At various times post-administration (e.g., 4, 8, 16, 32, 64 days, etc.), mice are sacrificed and autopsies performed to determine transgene expression in various host cells and tissues. The onset, kinetics and persistence of expression are also evaluated and compared for the wtAAV and double-stranded vectors. Of particular interest are cells that are typically refractory to wtAAV vectors such as bone marrow stem cells, astrocytes, and pulmonary epithelial cells. Also of interest are non-replicating or slowly-replicating cells that inefficiently support second-strand AAV synthesis such as muscle, liver and cells of the central nervous system.

Although the foregoing invention has been described in some detail by way of illustration and example for purposes of clarity and understanding, it will be apparent that certain changes and modifications may be practiced within the scope of the appended claims and equivalents thereof.

That which is claimed is:

1. A parvovirus particle comprising:
   a parvovirus capsid; and
   a vector genome comprising in the 5' to 3' direction:
   (i) a 5' parvovirus terminal repeat;
   (ii) a first heterologous nucleotide sequence;
   (iii) a parvovirus terminal repeat modified such that resolution by Rep protein is reduced as compared with the 5' parvovirus terminal repeat and a 3' parvovirus terminal repeat;
   (iv) a separate heterologous nucleotide sequence; and
   (v) the 3' parvovirus terminal repeat;
   wherein the first and the separate heterologous nucleotide sequences are essentially self-complementary and may form a hairpin structure.

2. The parvovirus particle of claim 1, wherein the 5' and 3' parvovirus terminal repeats are 5' and 3' adeno-associated virus (AAV) terminal repeats.

3. The parvovirus particle of claim 2, wherein the 5' and 3' AAV terminal repeats are selected from the group consisting of 5' and 3' AAV1, AAV2, AAV3, AAV4, AAV5 and AAV6 terminal repeats.

4. The parvovirus particle of claim 1, wherein the modification such that resolution by Rep protein is reduced is an insertion, a deletion or a substitution.

5. The parvovirus particle of claim 1, wherein the modification such that resolution by Rep protein is reduced is an insertion, a deletion or a substitution in the nucleotide sequence of the terminal resolution site (trs).

6. The parvovirus particle of claim 1, wherein the modification such that resolution by Rep protein is reduced is a deletion of the trs.

7. The parvovirus particle of claim 6, wherein the modification such that resolution by Rep protein is reduced is a deletion of essentially all of the D element.

8. The parvovirus particle of claim 1, wherein the modification such that resolution by Rep protein is reduced is an insertion in the D element.

9. The parvovirus particle of claim 1, wherein the modification such that resolution by Rep protein is reduced is an insertion in the nucleotide sequence of the trs.

SEQUENCE LISTING

<160> NUMBER OF SEQ ID NOS: 1

<210> SEQ ID NO 1
<211> LENGTH: 175
<212> TYPE: DNA
<213> ORGANISM: Artificial sequence
<220> FEATURE:
<223> OTHER INFORMATION: Inverted terminal repeat from the AAV-2 vector
      plasmid pSub 201

<400> SEQUENCE: 1

```
ctacaaggaa cccctagtga tggagttggc cactccctct ctgcgcgctc gctcgctcac        60
tgaggccgcc cgggcaaagc ccgggcgtcg ggcgaccttt ggtcgcccgg cctcagtgag       120
cgagcgagcg cgcagagagg gagtggccaa ctccatcact aggggttcct tgtag           175
```

10. The parvovirus particle of claim 1, wherein the modification such that resolution by Rep protein is reduced is one or more nucleotide substitutions in the nucleotide sequence of the trs.

11. The parvovirus particle of claim 1, wherein the vector genome is approximately the size of the wild-type adeno-associated (AAV) genome.

12. The parvovirus particle of claim 1, wherein a polypeptide is encoded by the first and the separate heterologous nucleotide sequences.

13. The parvovirus particle of claim 12, wherein the polypeptide is a therapeutic polypeptide.

14. The parvovirus particle of claim 12, wherein the polypeptide is an immunogenic polypeptide.

15. The parvovirus particle of claim 12, wherein the polypeptide is an endostatin, an angiostatin, a superoxide dismutase, an erythropoietin, a monoclonal antibody, a Factor IX, a Factor X, a lysosomal enzyme, a globin, a leptin, a catalase, a tyrosine hydroxylase, a cytokine, a peptide growth factor, a hormone, a receptor, a suicide gene product, a tumor suppressor gene product or an ornithine transcarbamylase.

16. The parvovirus particle of claim 12, wherein the polypeptide is a cancer or a tumor antigen.

17. The parvovirus particle of claim 12, wherein the polypeptide is a bacterial antigen, a viral antigen, a protozoan antigen, or a parasite antigen.

18. The parvovirus particle of claim 1, wherein the first and the separate heterologous nucleotide sequences encode an antisense nucleic acid, a ribozyme, an RNA that effects spliceosome-mediated trans-splicing, an interfering RNA (RNAi), or a guide RNA.

19. The parvovirus particle of claim 1, wherein said parvovirus capsid is an adeno-associated virus (AAV) capsid.

20. The parvovirus particle of claim 19, wherein said parvovirus capsid is selected from the group consisting of an AAV1, AAV2, AAV3, AAV4, AAV5 and AAV6 capsid.

21. The parvovirus particle of claim 1, wherein the 5' and 3' halves of the vector genome are essentially completely complementary to each other.

22. A pharmaceutical formulation comprising a plurality of the parvovirus particles of claim 1 in a pharmaceutically acceptable carrier.

23. A parvovirus particle comprising:
an adeno-associated virus (AAV) capsid; and
a vector genome comprising in the 5' to 3' direction:
(a) a 5' AAV terminal repeat;
(ii) a first heterologous nucleotide sequence;
(iii) an AAV terminal repeat modified such that resolution by Rep protein is reduced as compared to the 5' AAV terminal repeat and a 3' AAV terminal repeat;
(iv) a separate heterologous nucleotide sequence; and
(v) the 3' AAV terminal repeat;
wherein the first and the separate heterologous nucleotide sequences are essentially self-complementary and may form a hairpin structure.

24. The parvovirus particle of claim 23, wherein the modification such that resolution by Rep protein is reduced is an insertion, a deletion or a substitution.

25. The parvovirus particle of claim 23, wherein the modification such that resolution by Rep protein is reduced is an insertion, a deletion or a substitution in the nucleotide sequence of the trs.

26. The parvovirus particle of claim 23, wherein the vector genome is approximately the size of the wild-type adeno-associated (AAV) genome.

27. The parvovirus particle of claim 23, wherein a polypeptide is encoded by the first and separate heterologous nucleotide sequences.

28. The parvovirus particle of claim 27, wherein the polypeptide is a therapeutic polypeptide.

29. The parvovirus particle of claim 27, wherein the polypeptide is an immunogenic polypeptide.

30. The parvovirus particle of claim 27, wherein the polypeptide is an endostatin, an angiostatin, a superoxide dismutase, an erythropoietin, a monoclonal antibody, a Factor IX, a Factor X, a lysosomal enzyme, globin, a leptin, a catalase, a tyrosine hydroxylase, a cytokine, a peptide growth factor, a hormone, a receptor, a suicide gene product, a tumor suppressor gene product or an ornithine transcarbamylase.

31. The parvovirus particle of claim 27, wherein the polypeptide is a cancer or a tumor antigen.

32. The parvovirus particle of claim 27, wherein the polypeptide is a bacterial antigen, a viral antigen, a protozoan antigen, or a parasite antigen.

33. The parvovirus particle of claim 23, wherein the first and separate heterologous nucleotide sequences encode an antisense nucleic acid, a ribozyme, an RNA that effects spliceosome-mediated trans-splicing, an interfering RNA (RNAi), or a guide RNA.

34. A pharmaceutical formulation comprising a plurality of the parvovirus particles of claim 23 in a pharmaceutically acceptable carrier.

35. A method of delivering the vector genome to a cell, comprising contacting the cell with the parvovirus particle according to claim 1 under conditions sufficient for the parvovirus particle to enter the cell.

36. The method of claim 35, wherein the cell is selected from the group consisting of a cancer cell, a tumor cell, a brain cell, a muscle cell, an airway epithelial cell, a liver cell, a dendritic cell, and an eye cell.

37. The method of claim 35, wherein a polypeptide is encoded by the first and separate heterologous nucleotide sequences.

38. The method of claim 37, wherein the polypeptide is a therapeutic polypeptide.

39. The method of claim 37, wherein the polypeptide is an immunogenic polypeptide.

40. The method of claim 37, wherein the polypeptide is an endostatin, an angiostatin, a superoxide dismutase, an erythropoietin, a monoclonal antibody, a Factor IX, a Factor X, a lysosomal enzyme, a globin, a leptin, a catalase, a tyrosine hydroxylase, a cytokine, a peptide growth factor, a hormone, a receptor, a suicide gene product, a tumor suppressor gene product or an ornithine transcarbamylase.

41. The method of claim 37, wherein the polypeptide is a cancer or a tumor antigen.

42. The method of claim 37, wherein the polypeptide is a bacterial antigen, a viral antigen, a protozoan antigen, or a parasite antigen.

43. The method of claim 35, wherein the vector genome encodes an antisense nucleic acid, a ribozyme, an RNA that effects spliceosome-mediated trans-splicing, an interfering RNA (RNAi), or a guide RNA.

44. The method of claim 35, wherein the parvovirus capsid is an adeno-associated virus (AAV) capsid.

45. The method of claim 35, wherein the 5' and 3' parvovirus terminal repeats are 5' and 3' adeno-associated virus (AAV) repeats.

46. A method of delivering the vector genome to a cell, comprising contacting the cell with the parvovirus particle according to claim 23 under conditions sufficient for the parvovirus particle to enter the cell.

* * * * *

UNITED STATES PATENT AND TRADEMARK OFFICE
CERTIFICATE OF CORRECTION

PATENT NO. : 7,790,154 B2
APPLICATION NO. : 11/655520
DATED : September 7, 2010
INVENTOR(S) : Samulski et al.

Page 1 of 1

It is certified that error appears in the above-identified patent and that said Letters Patent is hereby corrected as shown below:

On Title Page:
Item (73) Assignee: Please correct "Chapell Hill" to read -- Chapel Hill --

In the Specification:
Column 33, Sequence Listing, Line 51: Please delete and replace with the following:

<160> NUMBER OF SEQ ID NOS: 1

<210> SEQ ID NO 1
<211> LENGTH: 198
<212> TYPE: DNA
<213> ORGANISM: Artificial sequence
<220> FEATURE:
<223> OTHER INFORMATION: Inverted terminal repeat from the AAV-2 vector plasmid pSub 201

<400> SEQUENCE: 1
ttggccactc cctctctgcg cgctcgctcg ctcactgagg ccgcccgggc aaagcccggg        60
cgtcgggcga cctttggtcg cccggcctca gtgagcgagc gagcgcgcag agagggagtg       120
gccaactcca tcactagggg ttccttgtag ttaatgatta acccgccatg ctacttatct       180
acgtagccat gctctaga                                                     198

Signed and Sealed this
Fifteenth Day of February, 2011

David J. Kappos
*Director of the United States Patent and Trademark Office*

UNITED STATES PATENT AND TRADEMARK OFFICE
CERTIFICATE OF CORRECTION

PATENT NO. : 7,790,154 B2  
APPLICATION NO. : 11/655520  
DATED : September 7, 2010  
INVENTOR(S) : R. J. Samulski et al.

Page 1 of 1

It is certified that error appears in the above-identified patent and that said Letters Patent is hereby corrected as shown below:

In the Specification:

Column 1, Lines 16-20, Please replace paragraph to read as follows:

"This invention was made with government support under Grant Nos. HL51818, HL48347 and DK54419 awarded by the National Institutes of Health. The government has certain rights in the invention."

Signed and Sealed this
Twenty-fifth Day of June, 2013

Teresa Stanek Rea
*Acting Director of the United States Patent and Trademark Office*